(12) United States Patent
Chattopadhyay et al.

(10) Patent No.: US 11,767,564 B2
(45) Date of Patent: Sep. 26, 2023

(54) USE OF SDHA AS A PROGNOSTIC MARKER AND THERAPEUTIC TARGET IN UVEAL MELANOMA

(71) Applicant: Board of Regents, The University of Texas System, Austin, TX (US)

(72) Inventors: Chandrani Chattopadhyay, Houston, TX (US); Janos Roszik, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 198 days.

(21) Appl. No.: 16/759,265

(22) PCT Filed: Oct. 25, 2018

(86) PCT No.: PCT/US2018/057580
§ 371 (c)(1),
(2) Date: Apr. 24, 2020

(87) PCT Pub. No.: WO2019/084313
PCT Pub. Date: May 2, 2019

(65) Prior Publication Data
US 2020/0399704 A1    Dec. 24, 2020

Related U.S. Application Data

(60) Provisional application No. 62/578,042, filed on Oct. 27, 2017.

(51) Int. Cl.
*C12Q 1/6886* (2018.01)
*C12N 9/02* (2006.01)

(52) U.S. Cl.
CPC .......... *C12Q 1/6886* (2013.01); *C12N 9/001* (2013.01); *C12Q 2600/118* (2013.01); *C12Q 2600/158* (2013.01); *C12Y 103/05001* (2013.01)

(58) Field of Classification Search
None
See application file for complete search history.

(56) References Cited

U.S. PATENT DOCUMENTS

| | | | |
|---|---|---|---|
| 2006/0263786 A1* | 11/2006 | Sorek | C07K 14/4748 435/325 |
| 2014/0271545 A1 | 9/2014 | Cook et al. | |
| 2015/0159221 A1 | 6/2015 | Seeger et al. | |
| 2015/0159225 A1 | 6/2015 | Triozzi et al. | |
| 2015/0352378 A1 | 12/2015 | Suh et al. | |
| 2015/0361058 A1 | 12/2015 | Al-Abed | |
| 2016/0273052 A1 | 9/2016 | Cook et al. | |
| 2016/0362489 A1 | 12/2016 | Yang | |
| 2017/0175197 A1* | 6/2017 | Gatalica | G01N 33/57492 |
| 2018/0228740 A1* | 8/2018 | Zhang | A61K 31/245 |

FOREIGN PATENT DOCUMENTS

| | | |
|---|---|---|
| WO | WO 2014-022826 | 2/2014 |
| WO | WO 2014-158696 | 10/2014 |
| WO | WO 2017-004243 | 1/2017 |
| WO | WO 2017-053915 | 3/2017 |

OTHER PUBLICATIONS

Fulda et al. (Antioxidants and Redox signaling 2011 vol. 15 p. 2937) (Year: 2011).*
Chattopadhyay et al., "Altered mitochondrial activity in uveal melanoma cells with monosomy 3," Presentation, The University of Texas MD Anderson Cancer Center, Nov. 8, 2016.
Chattopadhyay et al., "Elevated Endogenous SDHA Drives Pathological Metabolism in Highly Metastatic Uveal Melanoma," *Invest Ophthalmol Vis Sci.*, 60(13):4187-4195, 2019.
Chattopadhyay et al., "Monosomy 3 uveal melanoma cells have a unique metabolic phenotype distinct from disomy 3," ARVO Annual Meeting Abstract, Program No. 2504, 2017.
De Moura et al., "Mitochondrial respiration—an important therapeutic target in melanoma," *PLoS ONE*, 7(8):e40690, 2012.
PCT International Preliminary Report on Patentability issued in International Application No. PCT/US2018/057580, dated May 7, 2020.
PCT International Search Report and Written Opinion issued in International Application No. PCT/US2018/057580, dated Feb. 27, 2019.
Pilarski et al., "BAP1 tumor predisposition syndrome," *Gene Reviews*, 2016.
Plasseraud et al., "Clinical performance and management outcomes with the decisionDx-UM gene expression profile test in a prospective multicenter study," *Journal of Oncology*, 2016:5325762, 2016.
Testa et al., "Connecting molecular pathways to hereditary cancer risk syndromes," *Am Soc Clin Oncol Educ Book*, 81-90, 2013.

* cited by examiner

*Primary Examiner* — Katherine D Salmon
(74) *Attorney, Agent, or Firm* — Parker Highlander PLLC

(57) ABSTRACT

Provided herein are methods for identifying expression of SDHA, MIF, and or monosomy 3 or disomy 3 status in sample to identify the sample as high-risk melanoma and/or the sensitivity to oxidative phosphorylation inhibitors. Also provided herein are methods for treating monosomy 3 uveal melanoma by administering a SDHA inhibitor in combination with an oxidative phosphorylation inhibitor.

18 Claims, 24 Drawing Sheets

| Cell line | Mutations/Aberrations |
|---|---|
| Mel202 | GNAQ, SF3B1 |
| 92.1 | GNAQ, EIF1AX |
| OMM1 | GNA11 |
| 39 | GNAQ |
| 79 | GNAQ, BAP1 |
| 196 | GNAQ, BAP1 |

FIG. 2A (Cont'd)

USE OF SDHA AS A PROGNOSTIC MARKER AND THERAPEUTIC TARGET IN UVEAL MELANOMA

The present application is a national phase application under 35 U.S.C. § 371 of International Application No. PCT/US2018/057580, filed Oct. 25, 2018, which claims the priority benefit of U.S. Provisional Applications Ser. No. 62/578,042, filed Oct. 27, 2017, the entire contents of each of which are being hereby incorporated by reference.

This invention was made with government support under grant number P50 CA093459 awarded by the National Institutes of Health. The government has certain rights in the invention.

BACKGROUND

1. Field

The present invention relates generally to the field of molecular biology and medicine. More particularly, it concerns methods for detecting SDHA expression and methods of treating uveal melanoma.

2. Description of Related Art

Uveal melanoma (UM) is the most frequent primary intraocular cancer in adults and about 50% of primary melanomas metastasize, preferentially in the liver with very poor prognosis. UM arises from melanocytes in the choroidal plexus of the eye and while deaths from primary disease are uncommon, half of UM patients succumb to the effects of metastatic disease. Once UM is metastatic, the median survival for patients is only 3-6 months. The important genetic alterations associated with poor prognosis in UM are BAP1 gene alterations and loss of an entire copy of chromosome 3 (i.e., monosomy 3, M3), which are often concurrent as BAP1 is encoded on chromosome 3. It is unknown whether monosomy 3 and BAP1 loss are independent or interdependent mechanisms. Monosomy 3 and BAP1 loss in primary uveal melanoma are highly associated with the development of metastatic disease and poor prognosis. However, there are currently no approved therapies for monosomy 3 metastatic uveal melanoma.

SUMMARY

In a first embodiment, the present disclosure provides in vitro methods for detecting the expression of succinate dehydrogenase complex flavoprotein subunit A (SDHA) in a sample comprising obtaining a sample from a subject diagnosed with or at risk for uveal melanoma; isolating RNA from the sample; and detecting an elevated expression of SDHA RNA (e.g., by performing RT-qPCR, RNA sequencing, or microarray analysis on the isolated RNA). In some aspects, the uveal melanoma is further defined as BAP1 loss and/or monosomy 3 uveal melanoma. In certain aspects, the subject is human.

In certain aspects, the sample is a tissue biopsy, fine needle aspirate, saliva, urine, or plasma. In some aspects, the tissue biopsy is further defined as formalin fixed paraffin embedded (FFPE) tissue. In specific aspects, the tissue biopsy is further defined as a tumor biopsy.

In additional aspects, the method further comprises detecting the expression of MIF. In some aspects, the method further comprises detecting the expression of one or more genes (e.g., 2, 3, 4, 5, 6, 7, 8, 9, 10, 11, 12, 13, 14, 15, 16, 17, 18, 19, 20, 21, 22, 23, 24, 25, 26, 27, or 28) selected from the group consisting of BAP1_varA, BAP1_varB, MGP, SPP1, CXCL14, CLCA2, S100A8, BTG1, SAP130, ARG1, KRT6B, GJA, ID2, EIF1B, S100A9, CRABP2, KRT14, ROBOT, RBM23, TACSTD2, DSC1, SPRR1B, TRIM29, AQP3, TYRP1, PPL, LTA4H, and CST6.

In some aspects, elevated expression of SDHA as compared to a control identifies the sample as a high-risk uveal melanoma sample. In certain aspects, elevated expression of SDHA as compared to a control identifies the sample as a monosomy 3 uveal melanoma sample. In some aspects, elevated expression of SDHA as compared to a control identifies the subject as resistant to an oxidative phosphorylation (OXPHOS) inhibitor and/or immune checkpoint inhibitor therapy. In particular aspects, the elevated expression of SDHA as compared to a control identifies the subject as at risk for decreased overall survival and/or metastasis.

In some aspects, the method further comprises detecting the sample as monosomy 3 uveal melanoma or disomy 3 uveal melanoma. In some aspects, a monosomy 3 uveal melanoma sample with elevated expression of SDHA as compared to a control identifies the subject as having a poor prognosis and/or low overall survival. In other aspects, a monosomy 3 uveal melanoma sample with decreased expression of SDHA as compared to a control identifies the subject as having a good prognosis and/or high overall survival. In certain aspects, disomy 3 uveal melanoma sample with decreased expression of SDHA identifies the subject as having a poor prognosis and/or low overall survival.

In certain aspects, the subject has previously been administered or is being administered an anti-cancer therapy. In particular aspects, the anti-cancer therapy is chemotherapy, immunotherapy, surgery, radiotherapy, or biotherapy. In specific aspects, the anti-cancer therapy is immunotherapy, such as immune checkpoint inhibitor therapy.

In some aspects, the method further comprises administering an OXPHOS inhibitor to the subject with elevated expression of SDHA. In certain aspects, the OXPHOS inhibitor is IACS-1131, IACS-10759, oligomycin, rotenone, or metformin. In specific aspects, the OXPHOS inhibitor is IACS-10759.

In another embodiment, there provided an in vitro method for detecting expression of SDHA and MIF in a sample comprising obtaining a sample; isolating RNA from the sample; and detecting gene expression (e.g., elevated expression) of SDHA and MIF in the sample (e.g., by performing RT-qPCR, RNA sequencing, or microarray analysis on the sample). In some aspects, the uveal melanoma is further defined as BAP1 loss and/or monosomy 3 uveal melanoma. In certain aspects, the subject is human.

In certain aspects, the sample is a tissue biopsy, fine needle aspirate, saliva, urine, or plasma. In particular aspects, the tissue biopsy is further defined as formalin fixed paraffin embedded (FFPE) tissue. In specific aspects, the tissue biopsy is further defined as a tumor biopsy.

In additional aspects, the method further comprises detecting the expression of one or more genes (e.g., 2, 3, 4, 5, 6, 7, 8, 9, 10, 11, 12, 13, 14, 15, 16, 17, 18, 19, 20, 21, 22, 23, 24, 25, 26, 27, or 28) selected from the group consisting of BAP1_varA, BAP1_varB, MGP, SPP1, CXCL14, CLCA2, S100A8, BTG1, SAP130, ARG1, KRT6B, GJA, ID2, EIF1B, S100A9, CRABP2, KRT14, ROBOT, RBM23, TACSTD2, DSC1, SPRR1B, TRIM29, AQP3, TYRP1, PPL, LTA4H, and CST6.

In some aspects, elevated expression of SDHA and MIF as compared to a control identifies the sample as a high-risk uveal melanoma sample. In certain aspects, elevated expression of SDHA and MIF as compared to a control identifies the sample as a monosomy 3 uveal melanoma sample. In some aspects, elevated expression of SDHA and MIF as compared to a control identifies the subject as resistant to an OXPHOS inhibitor and/or immune checkpoint inhibitor therapy. In certain aspects, the elevated expression of SDHA as compared to a control identifies the subject as at risk for decreased overall survival and/or metastasis.

In certain aspects, the subject has previously been administered or is being administered an anti-cancer therapy. In some aspects, the anti-cancer therapy is chemotherapy, immunotherapy, surgery, radiotherapy, or biotherapy. In particular aspects, the anti-cancer therapy is immunotherapy, such as immune checkpoint inhibitor therapy.

In some aspects, the method further comprises administering an OXPHOS inhibitor to the subject with elevated expression of SDHA. In certain aspects, the OXPHOS inhibitor is IACS-1131, IACS-10759, oligomycin, rotenone, or metformin.

In a further embodiment, there are provided methods of treating cancer in a subject comprising determining an expression level of SDHA in a patient sample; and administering an effective amount of an SDHA inhibitor and an OXPHOS inhibitor to the patient identified to have an elevated expression of SDHA. In some aspects, the cancer is uveal melanoma, such as metastatic melanoma. In certain aspects, the patient has monosomy 3 and/or BAP1 loss. In some aspects, the patient is human.

In some aspects, the SDHA inhibitor is an inhibitory nucleic acid, such as siRNA, shRNA, or miRNA. In certain aspects, the inhibitory nucleic acid may be administered using an expression vector, such as a viral vector.

In certain aspects, the OXPHOS inhibitor is IACS-1131, IACS-10759, oligomycin, rotenone, or metformin.

In some aspects, the SDHA inhibitor and OXPHOS inhibitor are delivered simultaneously. In certain aspects, the SDHA inhibitor is delivered prior to the OXPHOS inhibitor. In specific aspects, the SDHA inhibitor restores sensitivity to the OXPHOS inhibitor.

In additional aspects, the method further comprises administering at least one additional anti-cancer therapy. In some aspects, the at least on additional anti-cancer therapy is chemotherapy, immunotherapy, radiotherapy, or biotherapy. In particular aspects, the at least one additional anti-cancer therapy is immunotherapy. In specific aspects, the immunotherapy is an immune checkpoint inhibitor. In certain aspects, the immune checkpoint inhibitor is selected from an inhibitor of CTLA-4, PD-1, PD-L1, PD-L2, LAG-3, BTLA, B7H3, B7H4, TIM3, KIR, or A2aR. In some aspects, the immune checkpoint inhibitor is an anti-PD1 antibody and/or an anti-CTLA4 antibody. In particular aspects, the anti-PD1 antibody is nivolumab, pembrolizumab, pidillizumab, KEYTRUDA®, AMP-514, REGN2810, CT-011, BMS 936559, MPDL328OA or AMP-224. In some aspects, the anti-CTLA-4 antibody is tremelimumab, YERVOY®, or ipilimumab.

In another embodiment, there are provided compositions comprising an effective amount of an SDHA inhibitor and an OXPHOS inhibitor for the treatment of cancer in a subject, wherein the subject is identified to have an elevated expression of SDHA. In some aspects, the cancer is uveal melanoma. In particular aspects, the uveal melanoma is metastatic melanoma. In some aspects, the subject has monosomy 3 and/or BAP1 loss. In some aspects, the subject is human.

In some aspects, the SDHA inhibitor is an inhibitory nucleic acid. In certain aspects, the inhibitory nucleic acid is siRNA, shRNA, or miRNA.

In certain aspects, the OXPHOS inhibitor is IACS-1131, IACS-10759, oligomycin, rotenone, or metformin.

In a further embodiment, there are provided methods for treating a cancer in a subject comprising administering an effective amount of an SDHA inhibitor to the subject. In particular aspects, administering the SDHA inhibitor overcomes resistance to an OXPHOS inhibitor. In additional aspects, the method further comprises administering an OXPHOS inhibitor. In some aspects, the cancer is uveal melanoma. In particular aspects, the subject has monosomy 3 and/or BAP1 loss. In some aspects, the subject is human.

In some aspects, the SDHA inhibitor is an inhibitory nucleic acid. In particular aspects, the inhibitory nucleic acid is siRNA, shRNA, or miRNA. In some aspects, the OXPHOS inhibitor is IACS-1131, IACS-10759, oligomycin, rotenone, or metformin.

In specific aspects, the subject is identified to have increased expression of SDHA as compared to a control expression level. In some aspects, the increased expression of SDHA is measured by RT-qPCR, microarray analysis, western blot, ELISA, immunohistochemistry, or Nanostring nCounter assay.

In additional aspects, the method further comprises administering at least a second anti-cancer therapy. In some aspects, the anti-cancer therapy is chemotherapy, immunotherapy, surgery, radiotherapy, or biotherapy. In some aspects, the SDHA inhibitor, the OXPHOS inhibitor, and/or the at least a second anti-cancer therapy is administered orally, intravenously, intraperitoneally, intratracheally, intratumorally, intramuscularly, endoscopically, intralesionally, percutaneously, subcutaneously, topically, regionally, or by direct injection or perfusion. In some aspects, the SDHA inhibitor, the OXPHOS inhibitor, and/or at least one additional anti-cancer therapy are administered simultaneously. In certain aspects, the SDHA inhibitor is administered prior to the at least one additional anti-cancer therapy.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Uveal melanoma cell survival after treatment with OXPHOS inhibitor, IACS-1131. (FIG. 1B) SDHA mRNA expression in non-sun exposed skin, sun exposed skin from the Genotype-Tissue Expression (GTEx) database, and skin cutaneous melanoma and uveal melanoma tumors from the Cancer Genome Atlas (TCGA). SDHA is overexpressed in BAP1-low uveal melanoma. (FIG. 1C) Overexpression of SDHA in monosomy 3 (M3) uveal melanoma compared to disomy 3 (D3), and association of uveal melanoma survival with SDHA mRNA expression. (FIG. 1D) mRNA expression of SDHA in TCGA tumor (dark grey dots) and GTEx normal tissue (light grey) samples. For uveal melanoma, the monosomy 3 (M3) and disomy 3 (D3) groups are shown. Lines represent median expression. (FIG. 1E) Cellular staining of uveal melanoma tissue samples for SDHA expression. Chromogen staining represents SDHA and melanin is seen as dark regions. SDHA is highly expressed in uveal melanoma. (FIG. 1F) Association of uveal melanoma overall survival with SDHA expression. (low, medium, and high) and monosomy 3 or disomy 3 status in the TCGA. Sample counts are shown in parentheses. The results show that in addition to monosomy 3 and disomy 3 status, SDHA is an important factor for prediction of survival.

(FIG. 2A) Characterization of uveal melanoma cell lines with T200.2 sequencing. Left panel shows analysis of chromosome copy number to characterize monosomy 3, while right panel shows identification of known genetic mutations of UM. (FIG. 2B) BAP1 protein expression in uveal melanoma cells.

(FIG. 3A) Mito stress test analyzing mitochondrial energy metabolism of uveal melanoma cells. Mitochondrial reserve capacity of monosomy 3/BAP1 loss cells (left) or disomy 3/BAP1 normal (right) uveal melanoma cells. This shows monosomy 3 cells have a higher reserve capacity as compared to disomy 3 cells. (FIG. 3B) Immunofluorescence of mitochondrial content in uveal melanoma cells, showing higher number of active mitochondria in monosomy 3 cells. (FIG. 3C) A global metabolic profile of 200 metabolites analyzed and most increased and decreased metabolites as ratio of monosomy 3 uveal melanoma cells to disomy 3 uveal melanoma cells summarized. (FIG. 3D) SDHA expression upregulated in monosomy 3 uveal melanoma cell lines.

(FIG. 5A) Western blot of SDHA expression in Me1202 and 39 cell lines. (FIG. 5B) Percent of cells of Me1202 cells untreated or treated with control siRNA or SDHA siRNA. (FIG. 5C) Percent of cells of 39 cells untreated or treated with control siRNA or SDHA siRNA.

(FIG. 7A) Survival rate of uveal melanoma predicted using TCGA data. SDHA and MIF expression both above median is associated with lowest survival rate. SDHA and MIF both below median is associated with highest survival rate. SDHA below median and MIF above median expression is associated with the second lowest survival rate ($p<0.001$). (FIG. 7B) In vitro validation of association of SDHA and MIF expression with uveal melanoma cell survival.

(FIG. 8A) Seahorse mito stress test assay testing mitochondrial respiration to show untreated metastatic uveal melanoma cell line 39 has significantly higher reserve capacity than non-metastatic cell lines 92.1, OMM1, and Me1202. (FIG. 8B) Seahorse assay comparing mitochondrial and non-mitochondrial respiration to show metastatic uveal melanoma cell line 39 has significantly higher mitochondrial respiration than the non-metastatic cell lines 92.1, OMM1, and Me1202, while non-mitochondrial respiration is similar in both.

DESCRIPTION OF ILLUSTRATIVE EMBODIMENTS

Figure 1A:
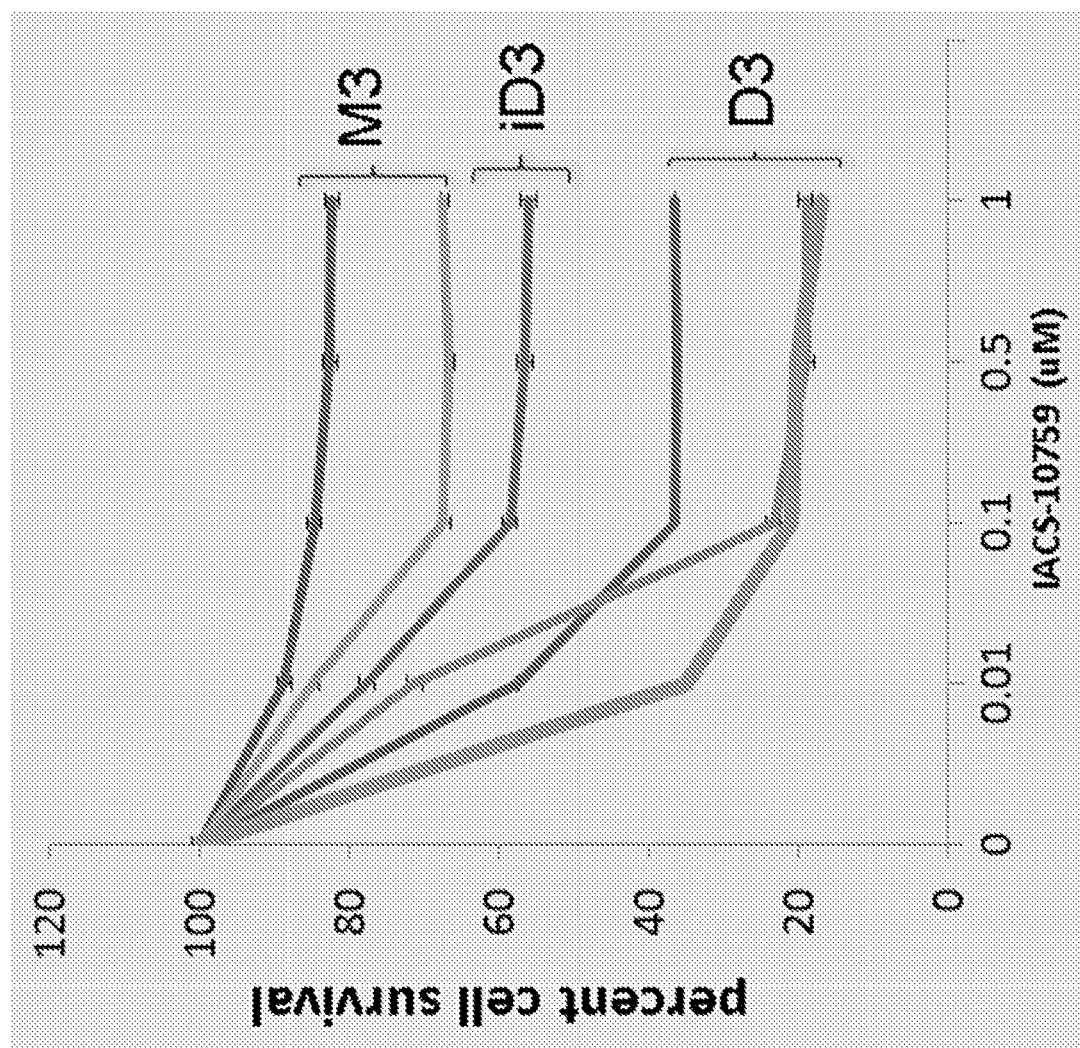
FIGS. 1A-1F.

Uveal melanoma patients with functional loss of BAP1 (localized in chromosome 3) and/or having a loss of a chromosome 3 copy are at a higher risk for metastasis with very poor prognosis, and these patients eventually die of liver metastasis. Loss of BAP1 protein is difficult to address therapeutically, as it represents a classic loss of a tumor suppressor, and direct therapies would require the re-establishment of wild type function. Monosomy 3 is a complete loss of an entire copy of chromosome 3 and cannot be reversed therapeutically using currently available gene therapy mechanisms.

In the present studies, a mitochondrial Oxidative Phosphorylation (OXPHOS) inhibitor, IACS-1131 or IACS-10759, was used to treat cells with or without monosomy 3. The results showed that cell lines with monosomy 3 are more resistant to this inhibitor compared to cell lines with normal chromosome 3. It was determined that BAP1 loss/monosomy 3 causes an aberrant mitochondrial metabolism in monosomy 3/BAP1 loss cells. Specifically, the monosomy 3 tumors express significantly higher levels of SDHA, an enzyme which connects the citric acid cycle to the mitochondrial electron transport chain. The present studies also found that high SDHA expression was associated with worse survival in uveal melanoma. siRNA knock down of SDHA in UM cells showed that overexpression of SDHA is the mechanistic reason for resistance to OXPHOS inhibitor therapy. Thus, SDHA may be an effective marker and therapy target in BAP1 loss/monosomy 3 uveal melanoma.

Accordingly, certain embodiments of the present disclosure provide methods for detecting the expression of SDHA in a sample. The sample may be obtained from the subject diagnosed with or at risk for uveal melanoma. Specifically, the subject may be diagnosed with BAP1 loss/monosomy 3 uveal melanoma. The SDHA may be detected by gene expression methods such as reverse transcription-quantitative real-time PCR (RT-qPCR), microarray analysis, Nanostring nCounter assay, picodroplet targeting and reverse transcription, or RNA sequencing. Other methods for detecting SDHA may include measuring proteins by immunoassays such as ELISA or western blot. An elevated expression of SDHA as compared to a control, such as a healthy subject, may indicate resistance to OXPHOS inhibition and/or immune checkpoint blockade therapy. The elevated expression may also indicate a subject with a poor prognosis, such as a decreased survival rate and/or increased rate of metastasis.

The methods may further comprise detecting expression of MIF in combination with expression of SDHA. In addition, the SDHA alone or in combination with MIF may be combined with expression of one or more genes, such as eight or more, from the genes BAP1_varA, BAP1_varB, MGP, SPP1, CXCL14, CLCA2, S100A8, BTG1, SAP130, ARG1, KRT6B, GJA, ID2, EIF1B, S100A9, CRABP2, KRT14, ROBOT, RBM23, TACSTD2, DSC1, SPRR1B, TRIM29, AQP3, TYRP1, PPL, LTA4H, and CST6 (e.g., described in U.S. Patent Publication No. US20160153042; incorporated herein by reference in its entirety).

Further provided herein are methods for treating a subject with uveal melanoma, such as monosomy 3 metastatic uveal melanoma. A patient identified to have elevated expression of SDHA alone or in combination with increased expression of MIF may be treated with a SDHA inhibitor in combination with an OXPHOS inhibitor (e.g., IACS-1131 or IACS-10759) and/or immune checkpoint blockade. The subject may have BAP1 loss and/or monosomy 3. The SDHA inhibitor may comprise inhibitory nucleic acids, such as siRNA or shRNA, antibodies, proteins, or other small molecule inhibitors. The patient may be further administered a MIF inhibitor, such as IOS-1, and/or additional anti-cancer therapies.

I. Definitions

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

The terms "about", "substantially" and "approximately" mean, in general, the stated value plus or minus 5%.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

As used herein, the term "therapeutically effective amount" refers to an amount of a therapeutic composition which confers a therapeutic effect on a treated subject, at a reasonable benefit/risk ratio applicable to any medical treatment. A therapeutic effect may be objective (i.e., measurable by some test or marker) or subjective (i.e., subject gives an indication of or feels an effect). In particular, a "therapeutically effective amount" refers to an amount of a therapeutic composition effective to treat, ameliorate, or prevent a desired disease or condition, or to exhibit a detectable therapeutic or preventative effect, such as by ameliorating symptoms associated with a disease, preventing or delaying onset of a disease, and/or also lessening severity or frequency of symptoms of a disease. A therapeutically effective amount is commonly administered in a dosing regimen that may comprise multiple unit doses. A therapeutically effective amount (and/or an appropriate unit dose within an effective dosing regimen) may vary, for example, depending on route of administration, combination with other agents, etc.

"Prognosis" refers to as a prediction of how a patient will progress, and whether there is a chance of recovery. "Cancer prognosis" generally refers to a forecast or prediction of the probable course or outcome of the cancer. As used herein, cancer prognosis includes the forecast or prediction of any one or more of the following: duration of survival of a patient susceptible to or diagnosed with a cancer, duration of recurrence-free survival, duration of progression-free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis and/or cancer progression in a patient susceptible to or diagnosed with a cancer. Prognosis also includes prediction of favorable survival following cancer treatments, such as a conventional cancer therapy.

As will be understood from context, a "risk" of a disease, disorder or condition comprises a likelihood that a particular individual will develop the disease, disorder, or condition.

As used herein, "metastasis" is defined as the recurrence or disease progression that may occur locally (such as local recurrence and in transit disease), regionally (such as nodal micrometastasis or macrometastasis), or distally (such as brain, lung and other tissues).

As used herein, "overall survival" (OS) refers to the percentage of people in a study or treatment group who are still alive for a certain period of time after they were diagnosed with or started treatment for a disease, such as cancer. The overall survival rate is often stated as a five-year survival rate, which is the percentage of people in a study or treatment group who are alive five years after their diagnosis or the start of treatment.

The term "determining an expression level" as used herein means the application of a gene specific reagent such as a probe, primer or antibody and/or a method to a sample, for example a sample of the subject and/or a control sample, for ascertaining or measuring quantitatively, semi-quantitatively or qualitatively the amount of a gene or genes, for example the amount of mRNA. For example, a level of a gene can be determined by a number of methods including for example immunoassays including for example immunohistochemistry, ELISA, Western blot, immunoprecipitation and the like, where a biomarker detection agent such as an antibody for example, a labeled antibody, specifically binds the biomarker and permits for example relative or absolute ascertaining of the amount of polypeptide biomarker, hybridization and PCR protocols where a probe or primer or primer set are used to ascertain the amount of nucleic acid biomarker, including for example probe based and amplification based methods including for example microarray analysis, RT-PCR such as quantitative RT-PCR, serial analysis of gene expression (SAGE), Northern Blot, digital molecular barcoding technology, for example Nanostring: nCounter™ Analysis, and TaqMan quantitative PCR assays. Other methods of mRNA detection and quantification can be applied, such as mRNA in situ hybridization in formalin-fixed, paraffin-embedded (FFPE) tissue samples or cells. This technology is currently offered by the QuantiGene®ViewRNA (Affymetrix), which uses probe sets for each mRNA that bind specifically to an amplification system to amplify the hybridization signals; these amplified signals can be visualized using a standard fluorescence microscope or imaging system. This system for example can detect and measure transcript levels in heterogeneous samples; for example, if a sample has normal and tumor cells present in the same tissue section. As mentioned, TaqMan probe-based gene expression analysis (PCR-based) can also be used for measuring gene expression levels in tissue samples, and for example for measuring mRNA levels in FFPE samples. In brief, TaqMan probe-based assays utilize a probe that hybridizes specifically to the mRNA target. This probe contains a quencher dye and a reporter dye (fluorescent molecule) attached to each end, and fluorescence is emitted only when specific hybridization to the mRNA target occurs. During the amplification step, the exonuclease activity of the polymerase enzyme causes the quencher and the reporter dyes to be detached from the probe, and fluorescence emission can occur. This fluorescence emission is recorded and signals are measured by a detection system; these signal intensities are used to calculate the abundance of a given transcript (gene expression) in a sample.

The term "elevated expression" means an increase in mRNA production or protein production over that which is normally produced by non-cancerous cells. Non-cancerous cells for use in determining base-line expression levels can be obtained from cells surrounding a tumor, from other humans or from human cell lines. Any increase can have diagnostic value, but generally the mRNA or protein expression will be elevated at least about 3-fold, 5-fold, and in some cases up to about 100-fold over that found in non-cancerous cells.

The term "sample" as used herein includes any biological specimen obtained from a patient. Samples include, without limitation, whole blood, plasma, serum, red blood cells, white blood cells (e.g., peripheral blood mononuclear cells), ductal lavage fluid, nipple aspirate, lymph (e.g., disseminated tumor cells of the lymph node), bone marrow aspirate, saliva, urine, stool (i.e., feces), sputum, bronchial lavage fluid, tears, fine needle aspirate (e.g., harvested by fine needle aspiration that is directed to a target, such as a tumor, or is random sampling of normal cells, such as periareolar), any other bodily fluid, a tissue sample (e.g., tumor tissue) such as a biopsy of a tumor (e.g., needle biopsy) or a lymph node (e.g., sentinel lymph node biopsy), and cellular extracts thereof.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

The term "hybridize" refers to the sequence specific non-covalent binding interaction with a complementary nucleic acid. In an embodiment, the hybridization is under high stringency conditions. Appropriate stringency conditions which promote hybridization are known to those skilled in the art.

The term "probe" as used herein refers to a nucleic acid sequence that will hybridize to a nucleic acid target sequence. In one example, the probe hybridizes to an RNA product of the gene or a nucleic acid sequence complementary thereof. The length of probe depends on the hybridizing conditions and the sequences of the probe and nucleic acid target sequence. In one embodiment, the probe is at least 8, 10, 15, 20, 25, 50, 75, 100, 150, 200, 250, 400, 500 or more nucleotides in length.

As used herein, the terms "control" and "standard" refer to a specific value that one can use to determine the value obtained from the sample. In one embodiment, a dataset may be obtained from samples from a group of subjects known to have a melanoma type or subtype. The expression data of the genes in the dataset can be used to create a control (standard) value that is used in testing samples from new subjects. In such an embodiment, the "control" or "standard" is a predetermined value for each gene or set of genes obtained from subjects with uveal melanoma subjects whose gene expression values and tumor types are known.

As used herein, the term "OXPHOS inhibitor" refers to an agent that inhibits oxidative phosphorylation, for example, oxidative phosphorylation in the mitochondria, either by direct inhibition of proteins involved in oxidative phosphorylation, or by inhibition of expression of the proteins involved in oxidative phosphorylation.

II. Gene Expression

Certain embodiments of the present disclosure provide methods of determining the expression of SDHA in a sample, such as a patient sample. The patient may be diagnosed with or at risk for uveal melanoma, particularly metastatic uveal melanoma. The patient may have monosomy 3 or BAP1. The sample may be a tumor sample, such as a biopsy. The method may identify patients at risk for developing metastasis or having a poor overall survival if the patient sample is measured to have high expression of SDHA and/or macrophage migration inhibitor factor (MIF). The method may further comprise identifying the subject as resistant to OXPHOS inhibition and/or immune checkpoint inhibition if the sample is determined to have high expression of SDHA and/or MIF. High expression of SDHA and/or MIF may indicate decreased overall survival, decreased progression-free survival, poor prognosis, or increased risk of metastasis.

In some embodiments, detecting expression of may comprise detecting levels of cDNA or RNA. As discussed in more detail below, in some embodiments primers are used in quantitative reverse transcriptase PCR and microarray methods for the amplification and detection of SDHA or fragments thereof. In certain embodiments, gene expression can be analyzed using direct DNA expression in microarray, Sanger sequencing analysis, Northern blot, the NANOSTRING® technology, serial analysis of gene expression (SAGE), RNA-seq, tissue microarray, or protein expression with immunohistochemistry or western blot technique.

The sample may be obtained from a subject, such as an animal or human. The sample may comprise tissue or fluid. A sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, or collection of body fluid (e.g., blood, lymph, feces). The sample may be obtained by processing (e.g., by removing one or more components of and/or by adding one or more agents to) a primary sample. For example, processing may comprise filtering using a semi-permeable membrane. Such a processed sample may comprise, for example nucleic acids extracted from a sample or obtained by subjecting a primary sample to techniques such as amplification, isolation and/or purification of certain components.

A person skilled in the art will appreciate that a number of detection agents can be used to determine the expression of the genes. For example, to detect RNA products of the biomarkers, probes, primers, complementary nucleotide sequences or nucleotide sequences that hybridize to the RNA products can be used. To detect protein products of the biomarkers, ligands or antibodies that specifically bind to the protein products can be used.

A reference or control sequence, sample, population, agent or individual is one that is sufficiently similar to a particular sequence, sample, population, agent or individual of interest to permit a relevant comparison (i.e., to be comparable). In some embodiments, information about a reference sample is obtained simultaneously with information about a particular sample. In some embodiments, information about a reference sample is historical. In some embodiments, information about a reference sample is stored for example in a computer-readable medium. In some embodiments, comparison of a particular sample of interest with a reference sample establishes identity with, similarity to, or difference of a particular sample of interest relative to a reference. In some embodiments, a reference for a marker is based on levels measured in an individual or population of individuals (e.g., an average across the population of 5, 10, 20 or more individuals) who do not present with symptoms of the disease in question (e.g., colorectal cancer). In some embodiments, a reference for a marker comprises a historical reference level for the marker from the individual being characterized.

In some embodiments, a risk of cancer, such as uveal melanoma, comprises a risk from 1, 2, 3, 4, 5, 6, 7, 8, 9, 10, 15, 20, 25, 30, 35, 40, 45, 50, 55, 60, 65, 70, 75, 80, 85, 90, 95, 100, 1000% or more relative to a reference. In some embodiments, a reference comprises an average occurrence of uveal melanoma in a population. In some embodiments, a reference comprises a statistical occurrence of uveal melanoma deemed to be acceptable or unavoidable in a population by medical professionals.

In some embodiments, the subject is classified as having an elevated risk or incidence of uveal melanoma if the levels of SDHA are elevated relative to a reference. In some embodiments, the individual is classified as having an elevated risk of metastasis if the levels of SDHA are elevated relative to a reference.

In some embodiments, the subject is classified as having an elevated risk or incidence of uveal melanoma if the levels of SDHA and MIF are both elevated relative to a reference. In some embodiments, the individual is classified as having an elevated risk of metastasis if the levels of SDHA and MIF are both elevated relative to a reference.

In some of these aforementioned embodiments, SDHA levels are increased 1, 2, 3, 4, 5, 6, 7, 8, 9, 10, 15, 20, 25, 30, 35, 40, 45, 50, 55, 60, 65, 70, 75, 80, 85, 90, 95, 100, 1000% or more relative to a reference. In some embodiments, MIF levels are increased 1, 2, 3, 4, 5, 6, 7, 8, 9, 10, 15, 20, 25, 30, 35, 40, 45, 50, 55, 60, 65, 70, 75, 80, 85, 90, 95, 100, 1000% or more relative to a reference.

In additional embodiments, the assay may detect the expression levels of one or more additional genes such as BAP1_varA, BAP1varB, MGP, SPP1, CXCL14, CLCA1, S100A8, BTG1, SAP130, ARG1, KRT6B, GJA, ID2, EIF1B, S100A9, CRABP2, KRT14, ROBOT, RBM23, TACSTD2, DSC1, SPRR1B, TRIM29, AQP3, TYRP1, PPL, LTA4H, and CST6, such as described in U.S. Patent Publication No. 20140271545; incorporated herein by reference in its entirety. The expression of the uveal melanoma biomarker PRAME may also be assessed in the sample (Field et al., 2016). In some aspects, the expression of at least eight additional genes is measured by a level of fluorescence by a sequence detection system following RT-PCR of the at least eight genes. The gene expression may be used to determine a patient gene-expression profile signature, comparing the patient gene-expression profile signature to a gene-expression profile of a predictive training set, and providing an indication as to a risk of metastasis, overall survival or both when the patient gene expression profile indicates that the expression levels of at the least eight genes are altered in a predictive manner as compared to the gene expression profile of the predictive training set.

As defined herein, "predictive training set" means a cohort of tumors with known clinical metastatic outcome and known genetic expression profile, used to define/establish all other tumors, based upon the genetic expression profile of each, as a low-risk, class 1 tumor type or a high-risk, class 2 tumor type. Additionally, included in the predictive training set is the definition of "threshold points" points at which a classification of metastatic risk is determined, specific to each individual gene expression level.

As defined herein, "altered in a predictive manner" means changes in genetic expression profile that predict metastatic risk or predict overall survival. Predictive modeling risk assessment can be measured as: 1) a binary outcome having risk of metastasis or overall survival that is classified as low risk (e.g., termed Class 1 herein) vs. high risk (e.g., termed Class 2 herein); and/or 2) a linear outcome based upon a probability score from 0 to 1 that reflects the correlation of the genetic expression profile of a cutaneous melanoma tumor with the genetic expression profile of the samples that comprise the training set used to predict risk outcome. Within the probability score range from 0 to 1, a probability score, for example, less than 0.5 reflects a tumor sample with a low risk of metastasis or death from disease, while a probability score, for example, greater than 0.5 reflects a tumor sample with a high risk of metastasis or death from disease. The increasing probability score from 0 to 1 reflects incrementally declining metastasis free survival.

The method may comprise assigning a low or high risk of metastasis. Low risk of metastasis may refer to 5-yr metastasis free survival rates of greater than 50%, 55%, 60%, 65%, 70%, 75%, 80%, 85%, 90%, 95% or more, and high risk of metastasis may refer to a 5-yr metastasis free survival rates of less than 50%, 45%, 40%, 35%, 30%, 25%, 20%, 15%, 10%, 5% or less.

A. Isolation of RNA

Aspects of the present disclosure concern the isolation of RNA from a patient sample for use in determining the expression of SDHA. The expression of MIF and/or other genes associated with uveal melanoma may also be assessed from the isolated RNA. The patient sample may blood, saliva, urine, or a tissue biopsy. The tissue biopsy may be a tumor biopsy that has been flash-frozen (e.g. in liquid nitrogen), formalin-fixed and paraffin-embedded (FFPE), and/or preserved by a RNA stabilization agent (e.g., RNAlater). In some aspects, isolation is not necessary, and the assay directly utilizes RNA from within a homogenate of the tissue sample. In certain aspects the homogenate of FFPE tumor sample is enzymatically digested.

RNA may be isolated using techniques well known to those of skill in the art. Methods generally involve lysing the cells with a chaotropic (e.g., guanidinium isothiocyanate) and/or detergent (e.g., N-lauroyl sarcosine) prior to implementing processes for isolating particular populations of RNA. Chromatography is a process often used to separate or isolate nucleic acids from protein or from other nucleic acids. Such methods can involve electrophoresis with a gel matrix, filter columns, coated magnetic beads, alcohol precipitation, and/or other chromatography.

B. Expression Assessment

In certain aspects, methods of the present disclosure concern measuring expression of gene(s) such as SDHA as well as one or more reference genes in a sample from a subject with or at risk for uveal melanoma. The expression information may be obtained by testing cancer samples by a lab, a technician, a device, or a clinician.

Expression levels of the gene(s) can be detected using any suitable means known in the art. For example, detection of gene expression can be accomplished by detecting nucleic acid molecules (such as RNA) using nucleic acid amplification methods (such as RT-PCR, droplet-based RT amplification, exon capture of RNA sequence library, next generation RNA sequencing), array analysis (such as microarray analysis), or hybridization methods (such as ribonuclease protection assay, bead-based assays, or Nanostring®). Detection of gene expression can also be accomplished using assays that detect the proteins encoded by the genes, including immunoassays (such as ELISA, Western blot, RIA assay, or protein arrays).

The pattern or signature of expression in each sample may then be used to generate a cancer prognosis or classification, such as predicting cancer survival or recurrence, using the expression of SDHA alone or in combination with other genes, such as MIF. The expression of one or more of genes could be assessed to predict or report prognosis or prescribe treatment options for cancer patients, especially uveal melanoma patients.

The expression of one or more genes may be measured by a variety of techniques that are well known in the art. Quantifying the levels of the messenger RNA (mRNA) of a gene may be used to measure the expression of the gene. Alternatively, quantifying the levels of the protein product of genes may be to measure the expression of the genes. Additional information regarding the methods discussed below may be found in Ausubel et al., (2003) Current Protocols in Molecular Biology, John Wiley & Sons, New York, N.Y., or Sambrook et al. (1989) Molecular Cloning: A Laboratory Manual, Cold Spring Harbor Press, Cold Spring Harbor, N.Y. One skilled in the art will know which parameters may be manipulated to optimize detection of the mRNA or protein of interest.

A nucleic acid microarray may be used to quantify the differential expression of SDHA and, optionally, one or more additional genes. Microarray analysis may be performed using commercially available equipment, following manufacturer's protocols, such as by using the Affymetrix GeneChip® technology (Santa Clara, Calif.) or the Microarray System from Incyte (Fremont, Calif.). Typically, single-stranded nucleic acids (e.g., cDNAs or oligonucleotides) are plated, or arrayed, on a microchip substrate. The arrayed sequences are then hybridized with specific nucleic acid probes from the cells of interest. Fluorescently labeled cDNA probes may be generated through incorporation of fluorescently labeled deoxynucleotides by reverse transcription of RNA extracted from the cells of interest. Alternatively, the RNA may be amplified by in vitro transcription and labeled with a marker, such as biotin. The labeled probes are then hybridized to the immobilized nucleic acids on the microchip under highly stringent conditions. After stringent washing to remove the non-specifically bound probes, the chip is scanned by confocal laser microscopy or by another detection method, such as a CCD camera. The raw fluorescence intensity data in the hybridization files are generally preprocessed with a robust statistical normalization algorithm to generate expression values.

Quantitative real-time PCR (qRT-PCR) may also be used to measure the differential expression of one or more genes. In qRT-PCR, the RNA template is generally reverse transcribed into cDNA, which is then amplified via a PCR reaction. The amount of PCR product is followed cycle-by-cycle in real time, which allows for determination of the initial concentrations of mRNA. To measure the amount of PCR product, the reaction may be performed in the presence of a fluorescent dye, such as SYBR Green, which binds to double-stranded DNA. The reaction may also be performed with a fluorescent reporter probe that is specific for the DNA being amplified.

For example, extracted RNA can be reverse-transcribed using a GeneAmp® RNA PCR kit (Perkin Elmer, Calif., USA), following the manufacturer's instructions. In some embodiments, gene expression levels can be determined using a gene expression analysis technology that measure mRNA in solution. Methods of detecting gene expression are described for example in U. S. Patent Application Nos. US20140357660, and US20130259858; incorporated herein by reference. Examples of such gene expression analysis technologies include, but not limited to RNAscope™, RT-PCR, Nanostring®, QuantiGene®, gNPA®, HTG®, microarray, and sequencing. For example, methods of Nanostring use labeled reporter molecules, referred to as labeled "nanoreporters," that are capable of binding individual target molecules. Through the nanoreporters' label codes, the binding of the nanoreporters to target molecules results in the identification of the target molecules. Methods of Nanostring are described in U.S. Pat. No. 7,473,767 (see also, Geiss et al., 2008). Methods may include the RainDance droplet amplification method such as described in U.S. Pat. No. 8,535,889, incorporated herein by reference. Sequencing may include exon capture, such as Illumina targeted sequencing after the generation of a tagged library for next generation sequencing (e.g. described in International Patent Application No. WO2013131962, incorporated herein by reference).

A non-limiting example of a fluorescent reporter probe is a TaqMan® probe (Applied Biosystems, Foster City, Calif.). The fluorescent reporter probe fluoresces when the quencher is removed during the PCR extension cycle. Multiplex qRT-PCR may be performed by using multiple gene-specific reporter probes, each of which contains a different fluorophore. Fluorescence values are recorded during each cycle and represent the amount of product amplified to that point in the amplification reaction. To minimize errors and reduce any sample-to-sample variation, qRT-PCR is typically performed using a reference standard. The ideal reference standard is expressed at a constant level among different tissues, and is unaffected by the experimental treatment. The system can include a thermocycler, laser, charge-coupled device (CCD) camera, and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

To minimize errors and the effect of sample-to-sample variation, RT-PCR can be performed using an internal standard. The ideal internal standard is expressed at a constant level among different tissues, and is unaffected by an experimental treatment. RNAs commonly used to normalize patterns of gene expression are mRNAs for the housekeeping genes GAPDH, β-actin, and 18S ribosomal RNA.

A variation of RT-PCR is real time quantitative RT-PCR, which measures PCR product accumulation through a dual-labeled fluorogenic probe (e.g., TAQMAN® probe). Real time PCR is compatible both with quantitative competitive PCR, where internal competitor for each target sequence is used for normalization, and with quantitative comparative PCR using a normalization gene contained within the sample, or a housekeeping gene for RT-PCR (see Heid et al., 1996). Quantitative PCR is also described in U.S. Pat. No. 5,538,848. Related probes and quantitative amplification procedures are described in U.S. Pat. Nos. 5,716,784 and 5,723,591. Instruments for carrying out quantitative PCR in microtiter plates are available from PE Applied Biosystems (Foster City, Calif.).

The steps of a representative protocol for quantitating gene expression level using fixed, paraffin-embedded tissues as the RNA source, including mRNA isolation, purification, primer extension and amplification are given in various published journal articles (see Godfrey et al., 2000; Specht et al., 2001). Briefly, a representative process starts with cutting about 10 μm thick sections of paraffin-embedded neoplasm tissue samples or adjacent non-cancerous tissue. The RNA is then extracted, and protein and DNA are removed. Alternatively, RNA is isolated directly from a neoplasm sample or other tissue sample. After analysis of the RNA concentration, RNA repair and/or amplification steps can be included, if necessary, and RNA is reverse transcribed using gene specific primers, followed by preparation of a tagged RNA sequencing library, and paired-end sequencing. In another example, the RNA is not reverse transcribed, but is directly hybridized to a specific template and then labeled with oligonucleotides and/or chemical or fluorescent color to be detected and counted by a laser.

In some embodiments, the PCR reaction is used in a "single-plex" PCR assay. "Single-plex" refers to a single assay that is not carried out simultaneously with any other assays. Single-plex assays include individual assays that are carried out sequentially.

In some embodiments, the PCR reaction is used in a "multiplex" PCR assay. The term "multiplex" refers to multiple assays that are carried out simultaneously, in which detection and analysis steps are generally performed in parallel. Within the context of the present disclosure, a multiplex assay will include the use of the primers, alone or in combination with additional primers to identify, for example, SDHA and MIF simultaneously.

Immunohistochemical staining may also be used to measure the differential expression of one or more genes. This method enables the localization of a protein in the cells of a tissue section by interaction of the protein with a specific antibody. For this, the tissue may be fixed in formaldehyde or another suitable fixative, embedded in wax or plastic, and cut into thin sections (from about 0.1 mm to several mm thick) using a microtome. Alternatively, the tissue may be frozen and cut into thin sections using a cryostat. The sections of tissue may be arrayed onto and affixed to a solid surface (i.e., a tissue microarray). The sections of tissue are incubated with a primary antibody against the antigen of interest, followed by washes to remove the unbound antibodies. The primary antibody may be coupled to a detection system, or the primary antibody may be detected with a secondary antibody that is coupled to a detection system. The detection system may be a fluorophore or it may be an enzyme, such as horseradish peroxidase or alkaline phosphatase, which can convert a substrate into a colorimetric, fluorescent, or chemiluminescent product. The stained tissue sections are generally scanned under a microscope. Because a sample of tissue from a subject with cancer may be heterogeneous, i.e., some cells may be normal and other cells may be cancerous, the percentage of positively stained cells in the tissue may be determined. This measurement, along with a quantification of the intensity of staining, may be used to generate an expression value for the biomarker.

An enzyme-linked immunosorbent assay, or ELISA, may be used to measure the differential expression of one or more genes. There are many variations of an ELISA assay. All are based on the immobilization of an antigen or antibody on a solid surface, generally a microtiter plate. The original ELISA method comprises preparing a sample containing the biomarker proteins of interest, coating the wells of a microtiter plate with the sample, incubating each well with a primary antibody that recognizes a specific antigen, washing away the unbound antibody, and then detecting the antibody-antigen complexes. The antibody-antibody complexes may be detected directly. For this, the primary antibodies are conjugated to a detection system, such as an enzyme that produces a detectable product. The antibody-antibody complexes may be detected indirectly. For this, the primary antibody is detected by a secondary antibody that is conjugated to a detection system, as described above. The microtiter plate is then scanned and the raw intensity data may be converted into expression values using means known in the art.

An antibody microarray may also be used to measure the differential expression of one or more genes. For this, a plurality of antibodies is arrayed and covalently attached to the surface of the microarray or biochip. A protein extract containing the biomarker proteins of interest is generally labeled with a fluorescent dye.

The labeled gene protein(s) may be incubated with the antibody microarray. After washes to remove the unbound proteins, the microarray is scanned. The raw fluorescent intensity data may be converted into expression values using means known in the art.

Luminex multiplexing microspheres may also be used to measure the differential expression of a plurality of biomarkers. These microscopic polystyrene beads are internally color-coded with fluorescent dyes, such that each bead has a unique spectral signature (of which there are up to 100). Beads with the same signature are tagged with a specific oligonucleotide or specific antibody that will bind the target of interest (i.e., biomarker mRNA or protein, respectively). The target, in turn, is also tagged with a fluorescent reporter. Hence, there are two sources of color, one from the bead and the other from the reporter molecule on the target. The beads are then incubated with the sample containing the targets, of which up 100 may be detected in one well. The small size/surface area of the beads and the three-dimensional exposure of the beads to the targets allows for nearly solution-phase kinetics during the binding reaction. The captured targets are detected by high-tech fluidics based upon flow cytometry in which lasers excite the internal dyes that identify each bead and also any reporter dye captured during the assay. The data from the acquisition files may be converted into expression values using means known in the art.

In situ hybridization may also be used to measure the differential expression of a plurality of biomarkers. This method permits the localization of mRNAs of interest in the cells of a tissue section. For this method, the tissue may be frozen, or fixed and embedded, and then cut into thin sections, which are arrayed and affixed on a solid surface. The tissue sections are incubated with a labeled antisense probe that will hybridize with an mRNA of interest. The hybridization and washing steps are generally performed under highly stringent conditions. The probe may be labeled with a fluorophore or a small tag (such as biotin or digoxigenin) that may be detected by another protein or antibody, such that the labeled hybrid may be detected and visualized under a microscope. Multiple mRNAs may be detected simultaneously, provided each antisense probe has a distinguishable label. The hybridized tissue array is generally scanned under a microscope. Because a sample of tissue from a subject with cancer may be heterogeneous, i.e., some cells may be normal and other cells may be cancerous, the percentage of positively stained cells in the tissue may be determined. This measurement, along with a quantification of the intensity of staining, may be used to generate an expression value for each biomarker.

III. Methods of Use

Further provided herein are methods for treating or delaying progression of cancer, such as uveal melanoma, in a subject determined to have high expression of SDHA comprising administering to the subject an effective amount of a SDHA inhibitor. The subject may also be administered an OXPHOS inhibitor and/or an immune checkpoint inhibitor. In other embodiments, the method comprises treating cancer, such as uveal melanoma, in a subject determined to have low expression of SDHA (and thus sensitive to OXPHOS inhibition) comprising administering to the subject an effective amount of an OXPHOS inhibitor.

The SDHA inhibitor may comprise an inhibitory nucleic acid targeting SDHA. In particular aspects, the inhibitory nucleic acid comprises an antisense DNA. In some aspects, the inhibitory nucleic acid comprises is a dsRNA. In specific aspects, the inhibitory nucleic acid comprises siRNA, shRNA, or miRNA. The nucleic acid may be at least 15 base pairs in length, such as 19 to 25 base pairs in length. In other aspects, the nucleic acid is longer in length, such as at least 30 base pairs. Viral and non-viral based gene transfer methods can be used to introduce nucleic acids in cells. Viral vector delivery systems include DNA and RNA viruses, which have either episomal or integrated genomes after delivery to the cell. Methods of non-viral delivery of nucleic acids include lipofection, nucleofection, microinjection, biolistics, virosomes, liposomes, immunoliposomes, polycation or lipid:nucleic acid conjugates, naked DNA, artificial virions, and agent-enhanced uptake of DNA. Lipofection is described in (e.g., U.S. Pat. Nos. 5,049,386, 4,946,787; and 4,897,355) and lipofection reagents are sold commercially (e.g., Transfectam™ and Lipofectin™) Cationic and neutral lipids that are suitable for efficient receptor-recognition lipofection of polynucleotides include those of Feigner, WO 91117424. 91116024.

In some embodiments, the individual has cancer that is resistant (has been demonstrated to be resistant) to one or more anti-cancer therapies. For example, the uveal melanoma may be resistant to OXPHOS inhibition and/or immune checkpoint inhibition. In some embodiments, resistance to anti-cancer therapy includes recurrence of cancer or refractory cancer. Recurrence may refer to the reappearance of cancer, in the original site or a new site, after treatment. In some embodiments, resistance to anti-cancer therapy includes progression of the cancer during treatment with the anti-cancer therapy. In some embodiments, the cancer is at early stage or at late stage. In some aspects, the patient has been previously administered an anti-cancer therapy, such as a uveal melanoma therapy.

In some aspects, the SDHA inhibitor is administered in combination with at least one additional anti-cancer therapy. The SDHA inhibitor may be administered before, during, after, or in various combinations relative to the additional anti-cancer agent. The administrations may be in intervals ranging from concurrently to minutes to days to weeks. In embodiments where the SDHA inhibitor is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the SDHA inhibitor and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

The SDHA inhibitor and, optionally the anti-cancer agent, may be administered by the same route of administration or by different routes of administration. In some embodiments, the SDHA inhibitor and/or anti-cancer agent is administered intravenously, intramuscularly, subcutaneously, topically, orally, transdermally, intraperitoneally, intraorbitally, by implantation, by inhalation, intrathecally, intraventricularly, or intranasally. An effective amount of the SDHA inhibitor and/or anti-cancer agent may be administered for prevention or treatment of disease. The appropriate dosage of the SDHA inhibitor and anti-cancer agent be determined based on the type of disease to be treated, severity and course of the disease, the clinical condition of the individual, the individual's clinical history and response to the treatment, and the discretion of the attending physician.

A. OXPHOS Inhibitors

Oxidative phosphorylation (or OXPHOS in short) is the metabolic pathway in which cells use enzymes to oxidize nutrients, thereby releasing energy which is used to produce adenosine triphosphate (ATP). During oxidative phosphorylation, electrons are transferred from electron donors to electron acceptors such as oxygen, in redox reactions. These redox reactions release energy, which is used to form ATP.

Exemplary oxidative phosphorylation inhibitors that may be used in the present methods include but are not limited to IACS-1331, IACS-10759, oligomycin, malonate, oxaloacetate, barbiturates, rotenone, antimycin-A and arsenate. Suitable OXPHOS inhibitors may include inhibitors of mitochondrial OXPHOS, which may include biguanide compounds such as metformin, phenformin, buformin, and pharmaceutically acceptable salts thereof. In particular embodiments, the OXPHOS inhibitor is the clinically relevant inhibitor IACS-10759.

B. Pharmaceutical Compositions

Also provided herein are pharmaceutical compositions and formulations comprising the SDHA inhibitor, optionally an OXPHOS inhibitor, immune checkpoint inhibitor, and/or other anti-cancer agent and a pharmaceutically acceptable carrier.

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences 22nd edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

C. Anti-Cancer Therapy

In certain embodiments, the compositions and methods of the present embodiments involve SDHA inhibition in sequence or combination with at least additional anti-cancer agent. The additional therapy may be radiation therapy, surgery (e.g., lumpectomy and a mastectomy), chemotherapy, targeted molecular inhibitor, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant, neoadjuvant, or palliative therapy.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting receptor or receptor kinase signaling molecules, cyclin-dependent kinases or the cell cycle control, mTOR/PI3K pathway, HSP90 inhibitor, tubulin inhibitor, apoptosis inhibitor, and/or chemopreventative agent. The additional therapy may be one or more of the chemotherapeutic agents known in the art.

Various combinations may be employed. For the example below a SDHA inhibitor is "A" and an anti-cancer therapy is "B":

| A/B/A | B/A/B | B/B/A | A/A/B | A/B/B | B/A/A | A/B/B/B | B/A/B/B |
|-------|-------|-------|-------|-------|-------|---------|---------|
| B/B/B/A | | B/B/A/B | A/A/B/B | A/B/A/B | A/B/B/A | B/B/A/A | |
| B/A/B/A | | B/A/A/B | A/A/A/B | B/A/A/A | A/B/A/A | A/A/B/A | |

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclophosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaII and calicheamicin omegaI1); dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiatio, and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates have emerged as a breakthrough approach to the development of cancer therapeutics. Cancer is one of the leading causes of deaths in the world. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen (Leal et al., 2014). Targeted delivery of the drug also minimizes its exposure in normal tissues, resulting in decreased toxicity and improved therapeutic index. The approval of two ADC drugs, ADCETRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach (Teicher 2009) and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

In some embodiments, the immunotherapy may be an immune checkpoint inhibitor Immune checkpoints are molecules in the immune system that either turn up a signal (e.g., co-stimulatory molecules) or turn down a signal. Inhibitory checkpoint molecules that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAGS), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Pardoll 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present invention. For example it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Application No. 20140294898, 2014022021, and 20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence).

In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001014424, WO2000037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof. In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesions such as described in U.S. Pat. No. 8,329,867, incorporated herein by reference.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. Recently validated and approved clinical examples include the concurrent administration of hormonal therapy with a biotherapy that inhibits the cell cycle (e.g., palbociclib) or the mTOR/PI3K pathway (e.g., everolimus). Further examples can therefore be contemplated. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

IV. Articles of Manufacture or Kits

Further embodiments of the invention include kits for the measurement, analysis, and reporting of SDHA gene expression. A kit may include, but is not limited to microarray, quantitative RT-PCR, or other genomic platform reagents and materials, as well as hardware and/or software for performing at least a portion of the methods described. The kit may include nucleic acid probes or primers for the determining SDHA elevated expression of mRNA. For example, custom microarrays or analysis methods for existing microarrays are contemplated. Accordingly, an article of manufacture or a kit is provided comprising a customized assay for determining the expression of SDHA, MIF, and one or more genes is also provided herein. The article of manufacture or kit can further comprise a package insert comprising instructions for using the customized assay to determine gene expression and to then treat or delay progression of cancer, such as uveal melanoma, in an individual. Probes for any of the genes described herein may be included in the article of manufacture or kits. Suitable containers include, for example, bottles, vials, bags and syringes. The container may be formed from a variety of materials such as glass, plastic (such as polyvinyl chloride or polyolefin), or metal alloy (such as stainless steel or hastelloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. Suitable containers for the one or more agent include, for example, bottles, vials, bags and syringes.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—SDHA in Uveal Melanoma

It was hypothesized that monosomy 3 or BAP1 loss uveal melanoma cells have altered mitochondrial activity, specifically oxidative phosphorylation, that may contribute to metastasis, poor prognosis, and drug resistance of these cancer cells. Several uveal melanoma cell lines that have monosomy 3 or disomy 3 were evaluated for their sensitivity to an OXPHOS inhibitor, IACS-1131, at increasing concentrations from 0.01 µM to 1 µM. The disomy 3 cell lines responded to the OXPHOS inhibitor while the monosomy 3 cell lines were observed to have resistance to the inhibitor (FIG. 1A).

Figure 1B:
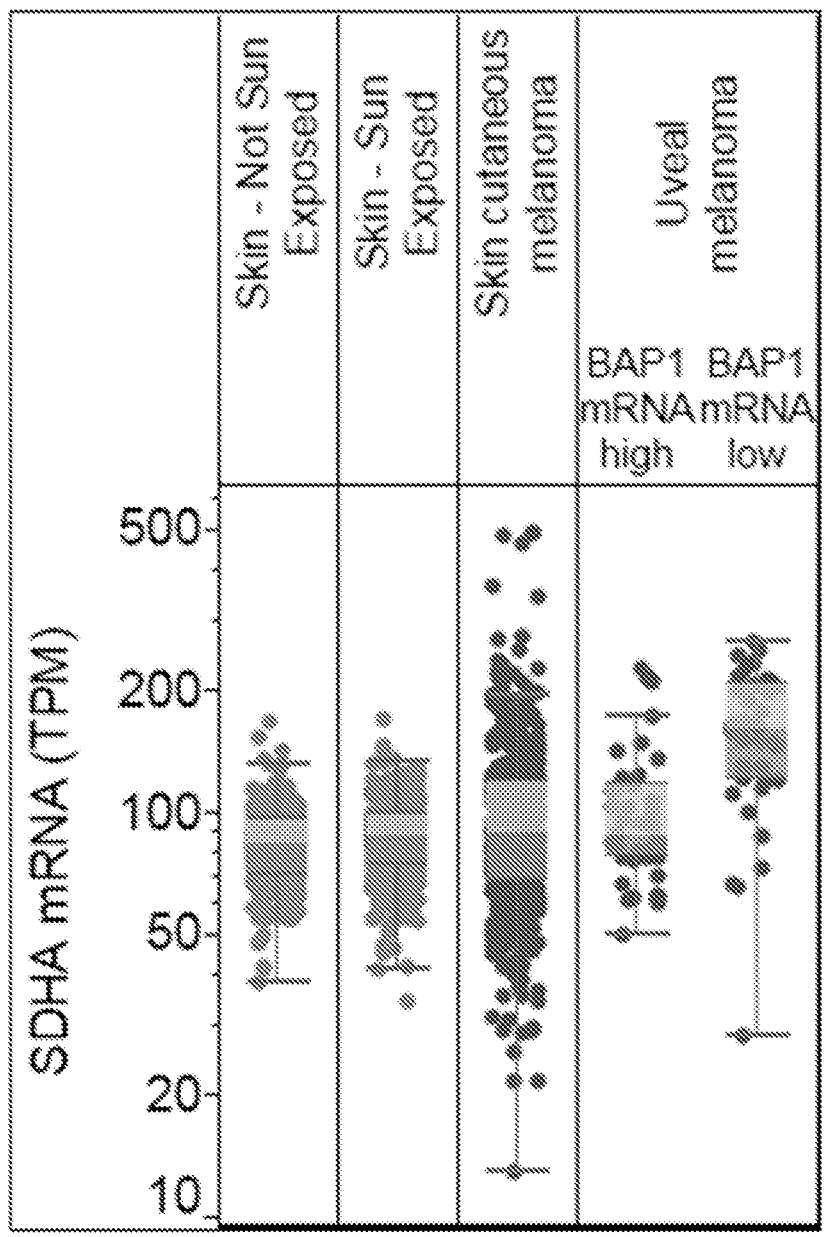
Figure 1C:
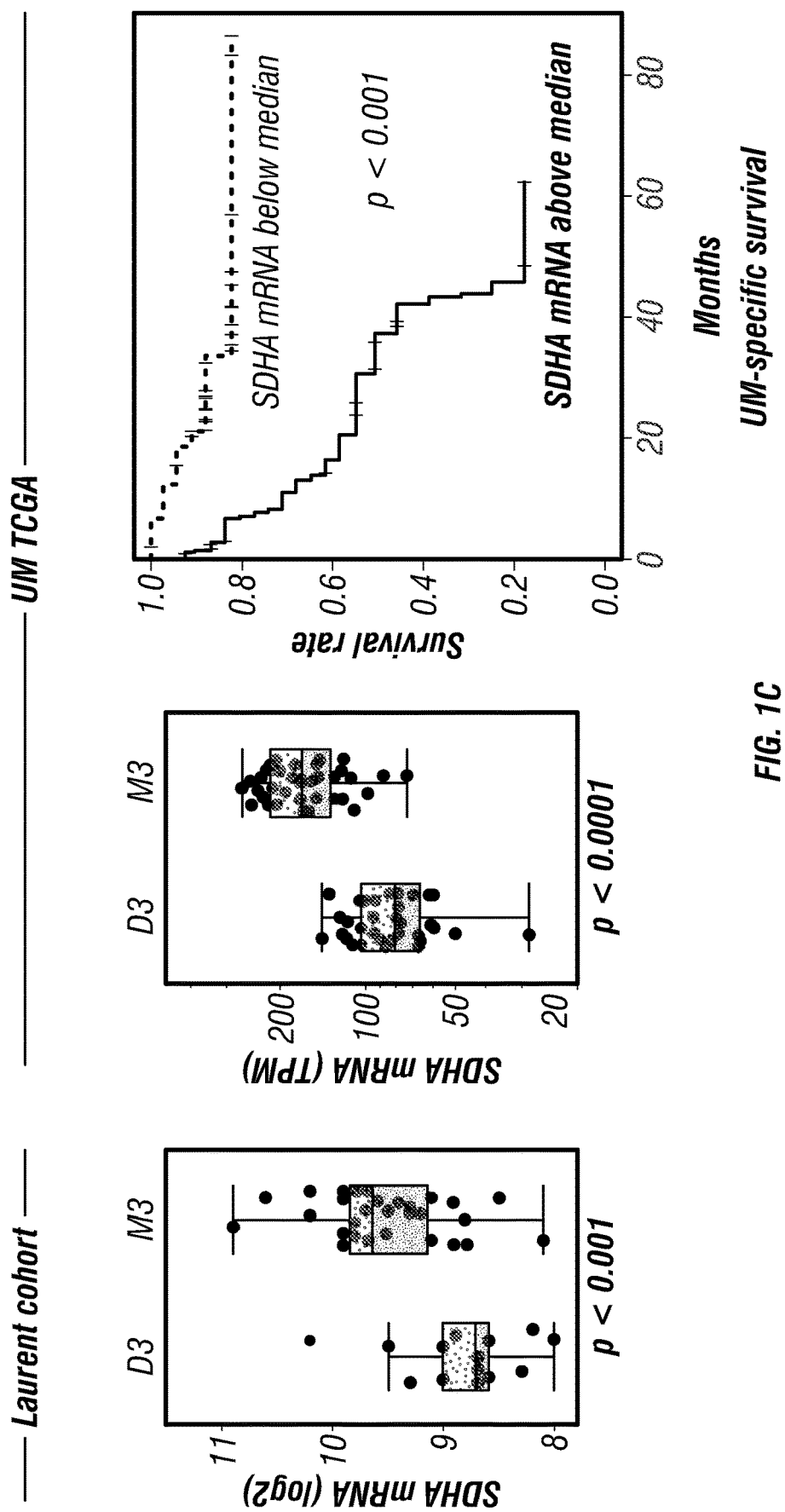
Figure 1D:
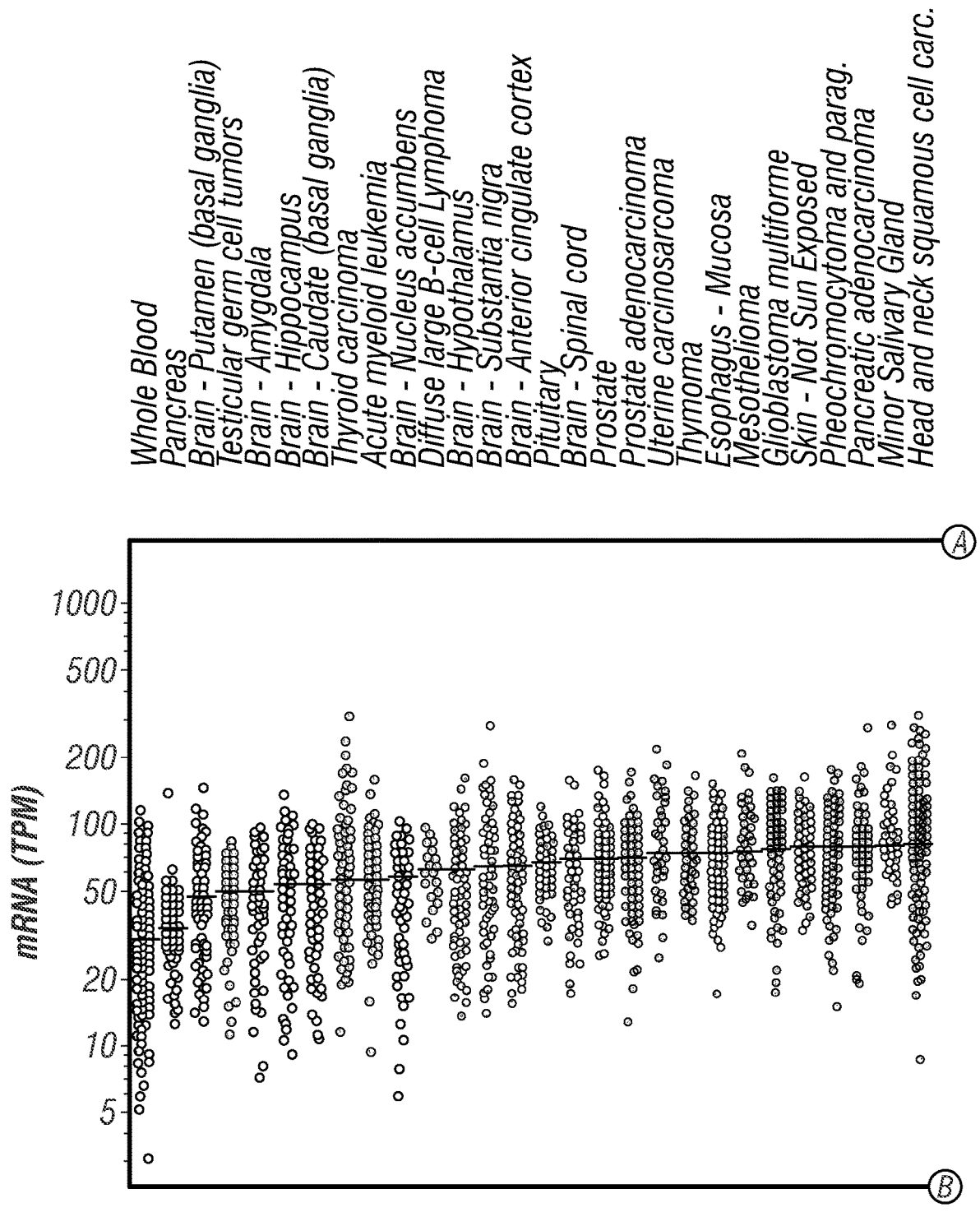
Figure 1D:
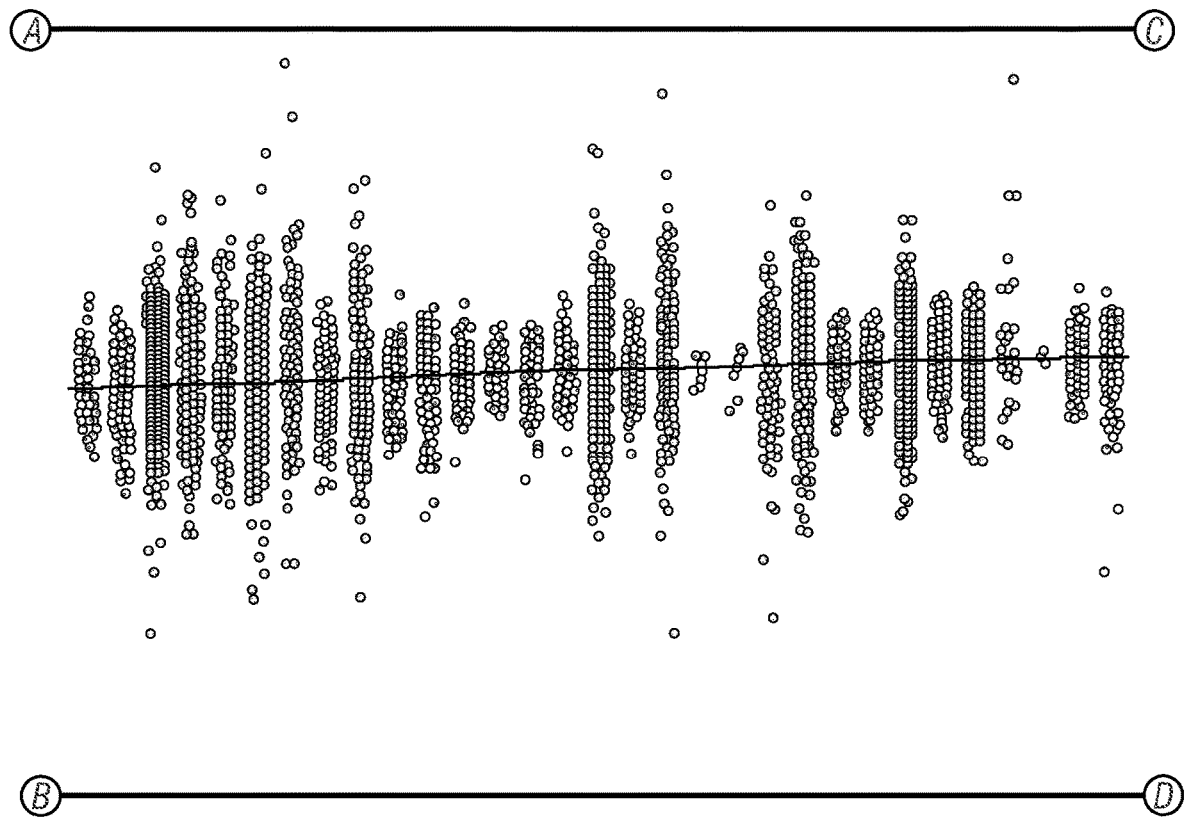
Figure 1D:
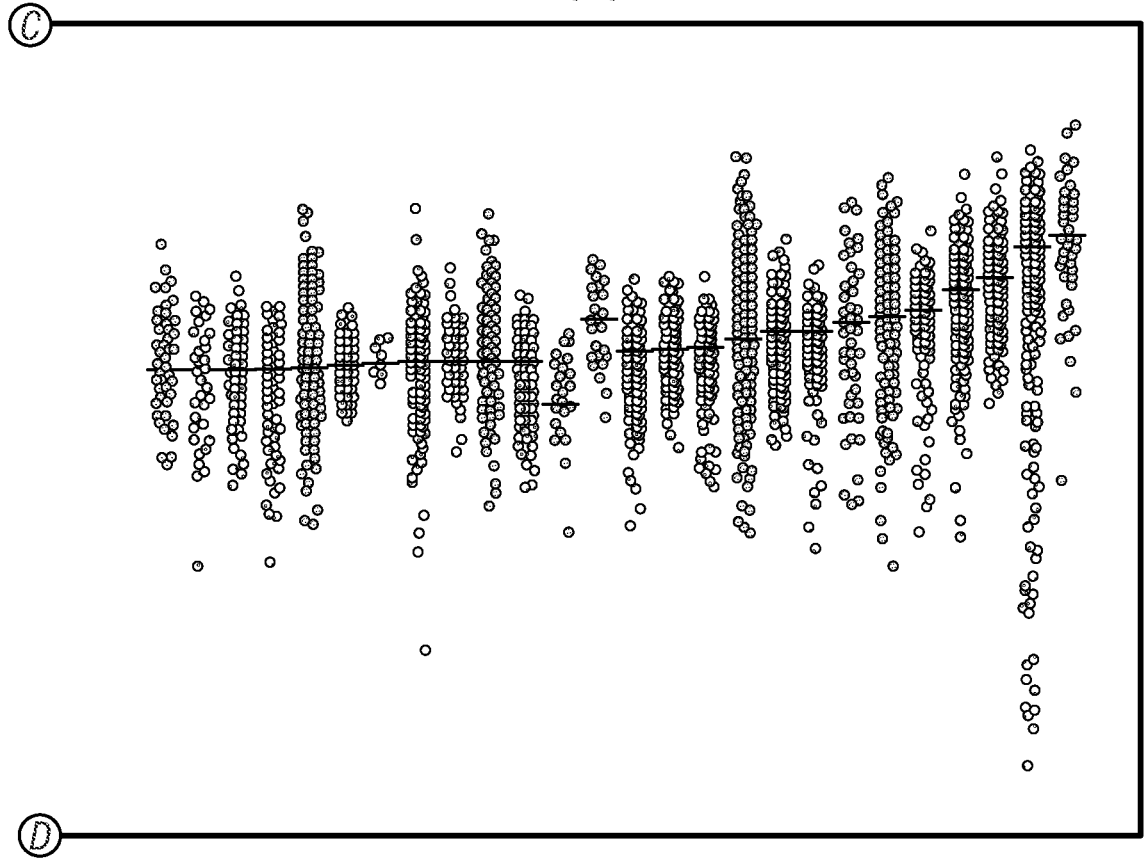
Figure 1E:
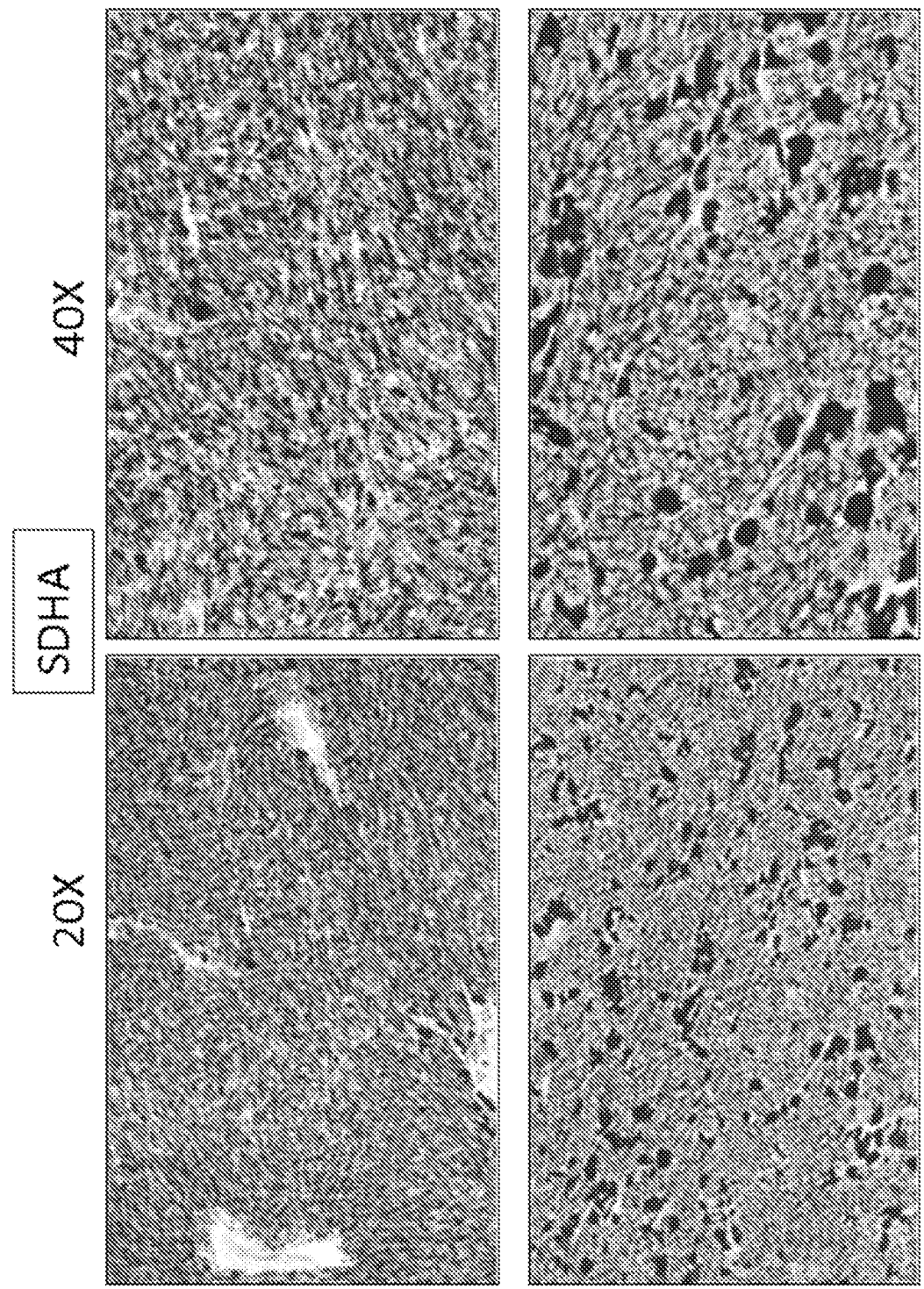
Figure 1F:
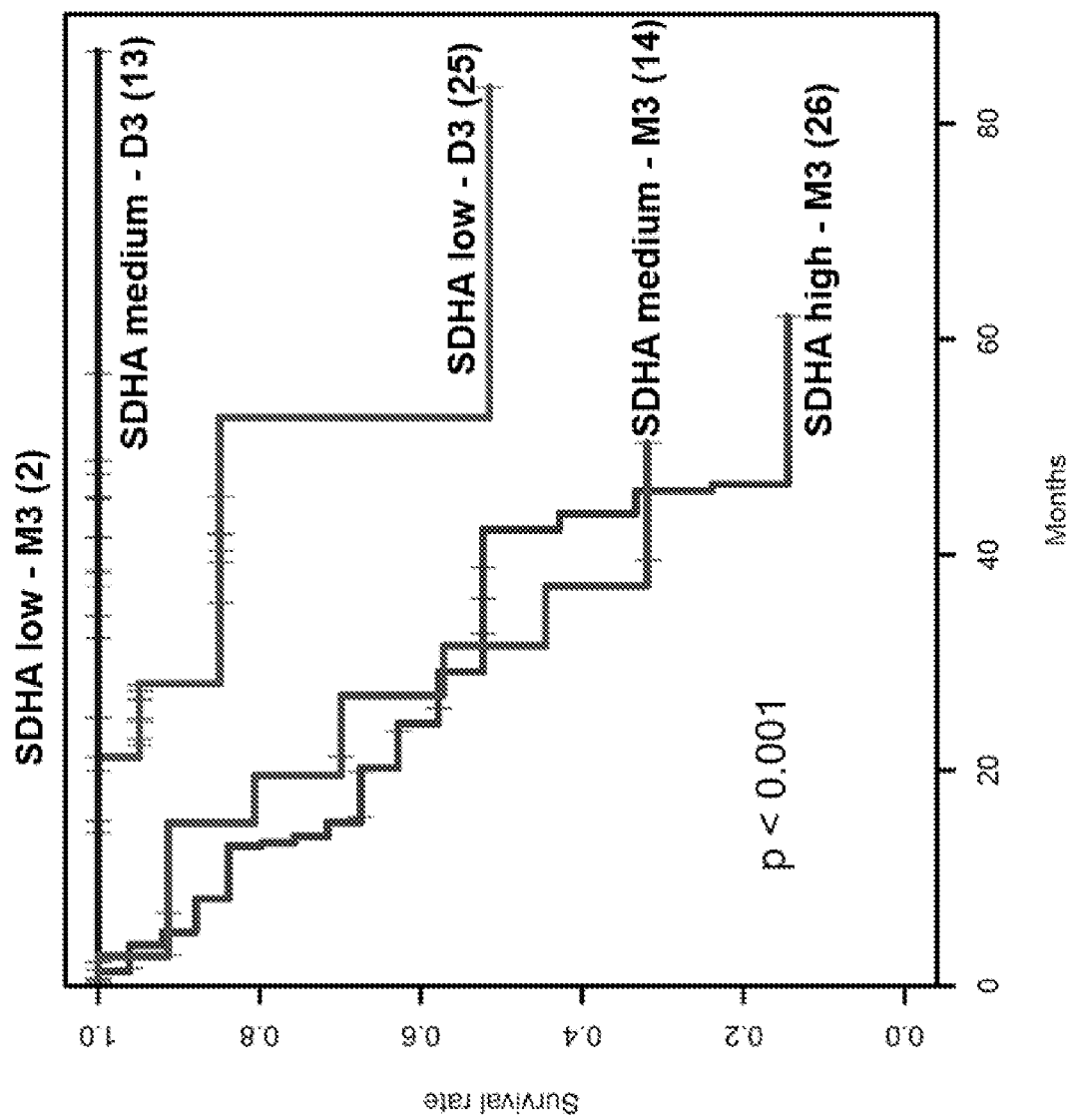

Thus, the expression of SDHA was analyzed in different cells including skin not exposed to the sun, skin exposed to the sun, skin cutaneous melanoma, and uveal melanoma with high or low BAP1 expression. It was found that uveal melanoma cells with low BAP1 expression were associated with high expression of SDHA (FIG. 1B). In addition, it was found that high SDHA expression is associated with shorter overall survival in uveal melanoma (FIG. 1C). Furthermore, it was found that uveal melanoma cells with monosomy 3 (M3) were associated with high expression of SDHA (FIG. 1D). Cellular staining of uveal melanoma tissue samples was performed for SDHA expression confirming that SDHA is highly expressed in uveal melanoma (FIG. 1E). It was also found that in combination with monosomy 3 (M3) and disomy 3 (D3) status SDHA expression level is an important predictor of survival (FIG. 1F).

Figure 2A:
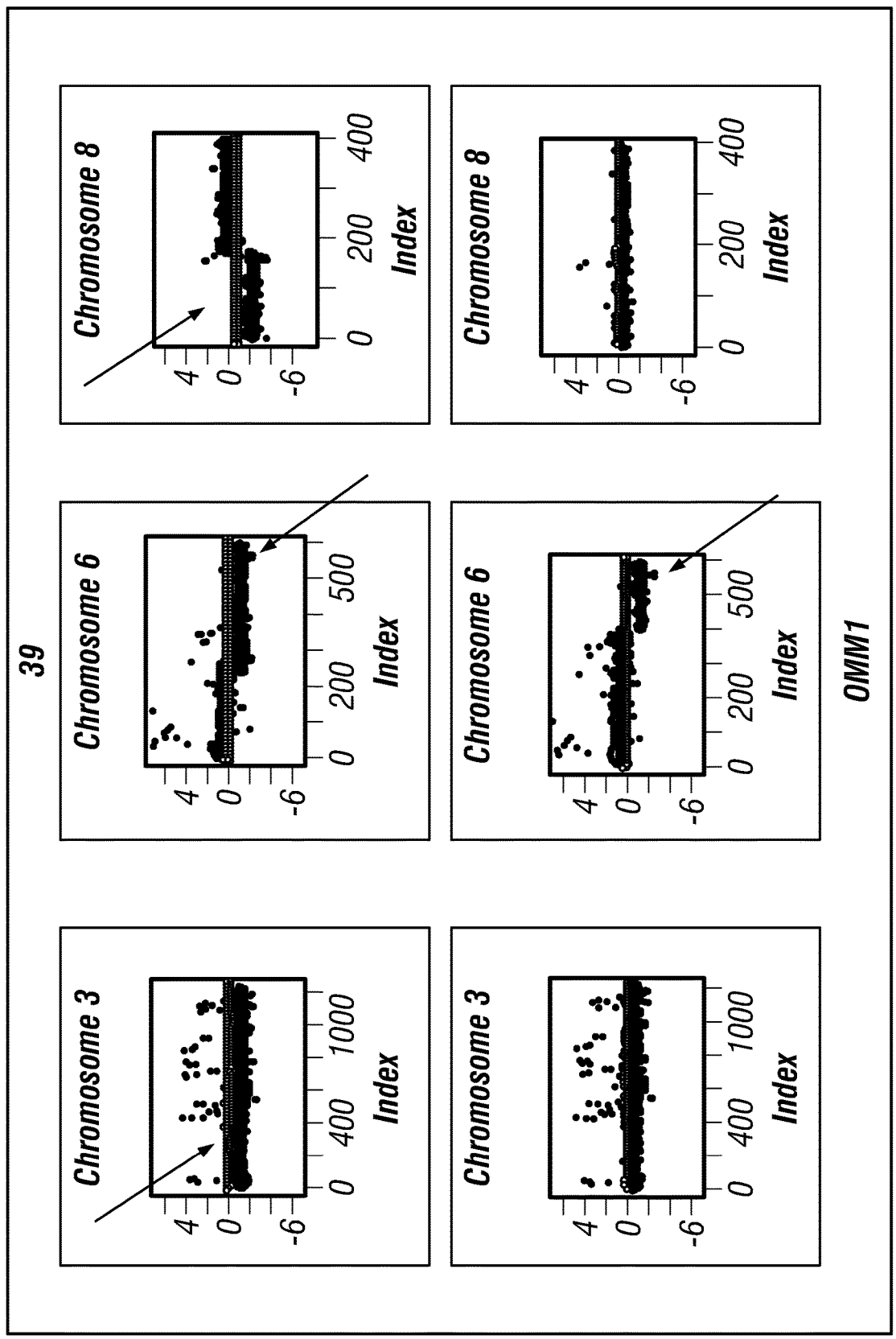
FIGS. 2A-2B.
Figure 2B:
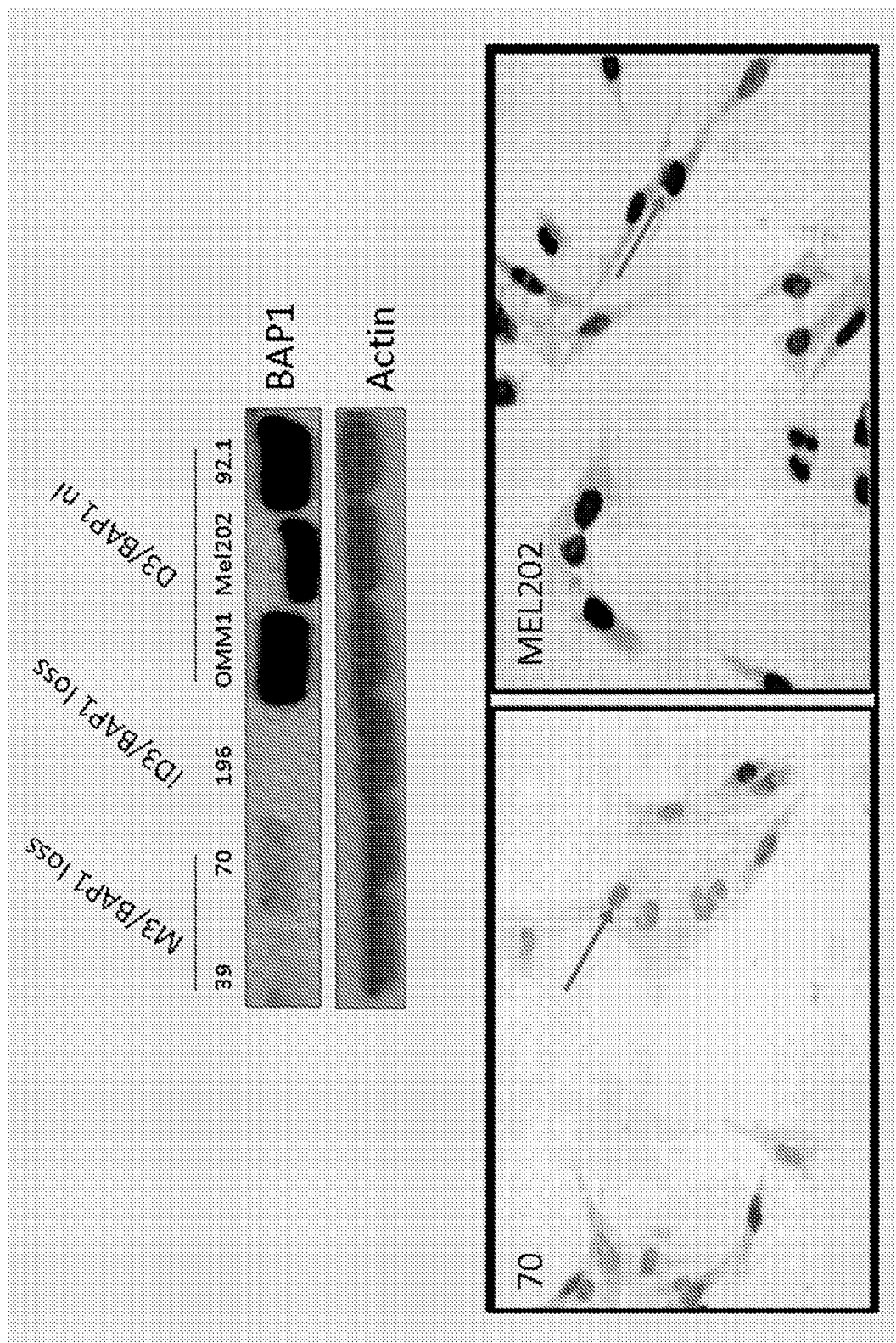

Several uveal melanoma cell lines were characterized by T200.2 sequencing at chromosome 3, 6, and 8. The cell lines included Me1202, 92.1, OMM1, 39, 70, and 196. The cell lines had mutations in GNAQ, GNA11, BAP1, SF3B1, or EIF1AX (FIG. 2A). The 39 and 70 cell lines had monosomy 3 while the other cell lines had disomy 3. Western blot analysis on the same cell lines showed BAP1 loss in the 39, 70, and 196 cell lines (FIG. 2B).

Cell survival analysis with monosomy and disomy 3 uveal melanoma cells in presence and absence of oxidative phosphorylation (OXPHOS) inhibitor, IACS-10759, was performed. Cells were cultured under ambient oxygen or 1% oxygen. Mitotracker Red dye staining was used to assay the extent of active mitochondria in monosomy 3 and disomy 3 cells. The percent cell survival of uveal melanoma cells treated with increasing concentrations of OXPHOS inhibitor, IACS-10759, was determined. Three UM cell lines with monosomy 3 were more resistant to IACS-10759 when compared to three lines with normal chromosome 3 copy number. This resistance diminishes under hypoxic conditions or in galactose media, when OXPHOS is not the predominant form of sugar metabolism. Thus, it was found that monosomy 3/BAP1 loss uveal melanoma cells are more resistant to inhibition of oxidative phosphorylation as compared to the disomy 3 cell lines.

Figure 3A:
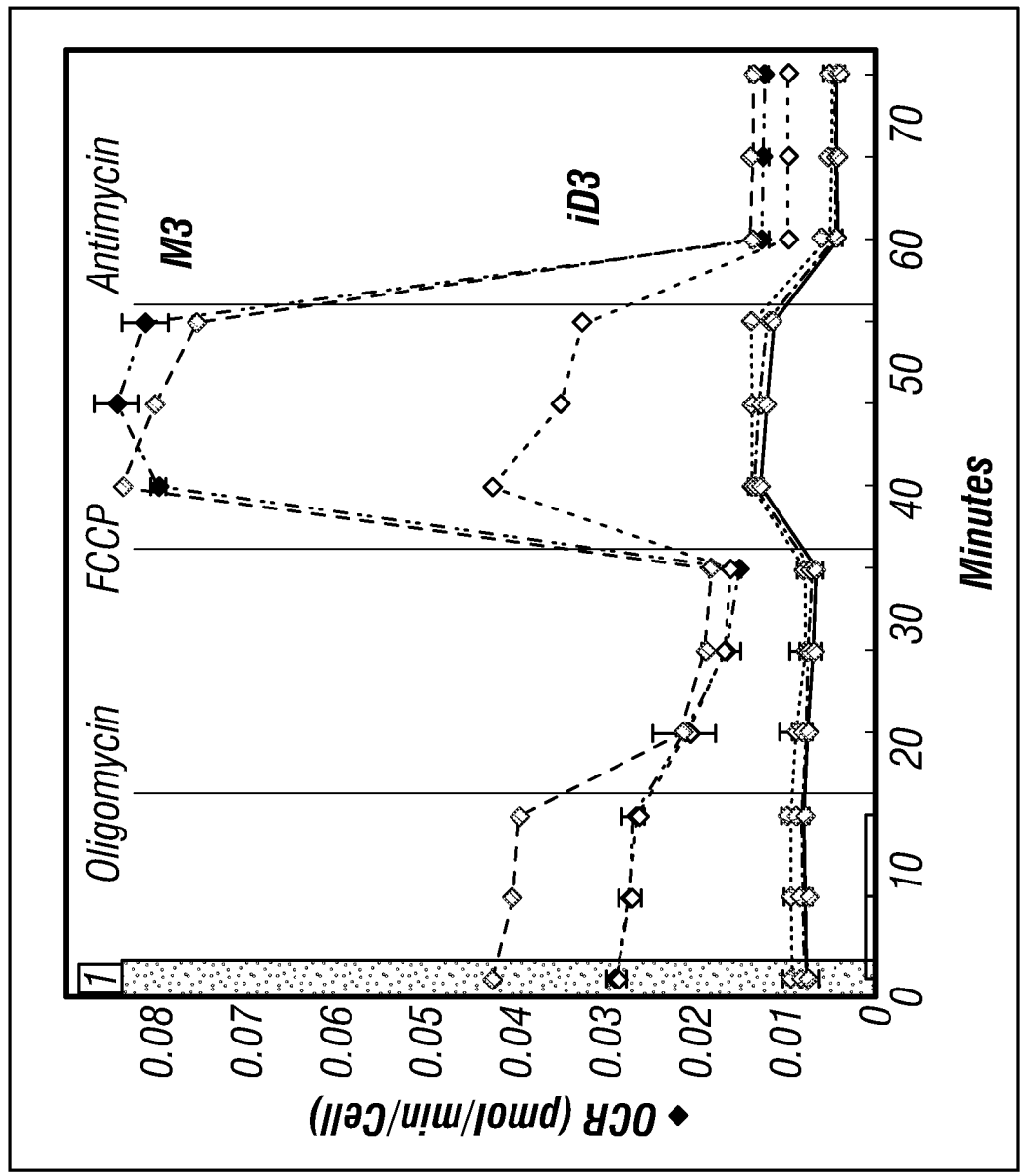
FIGS. 3A-3D.
Figure 3A:
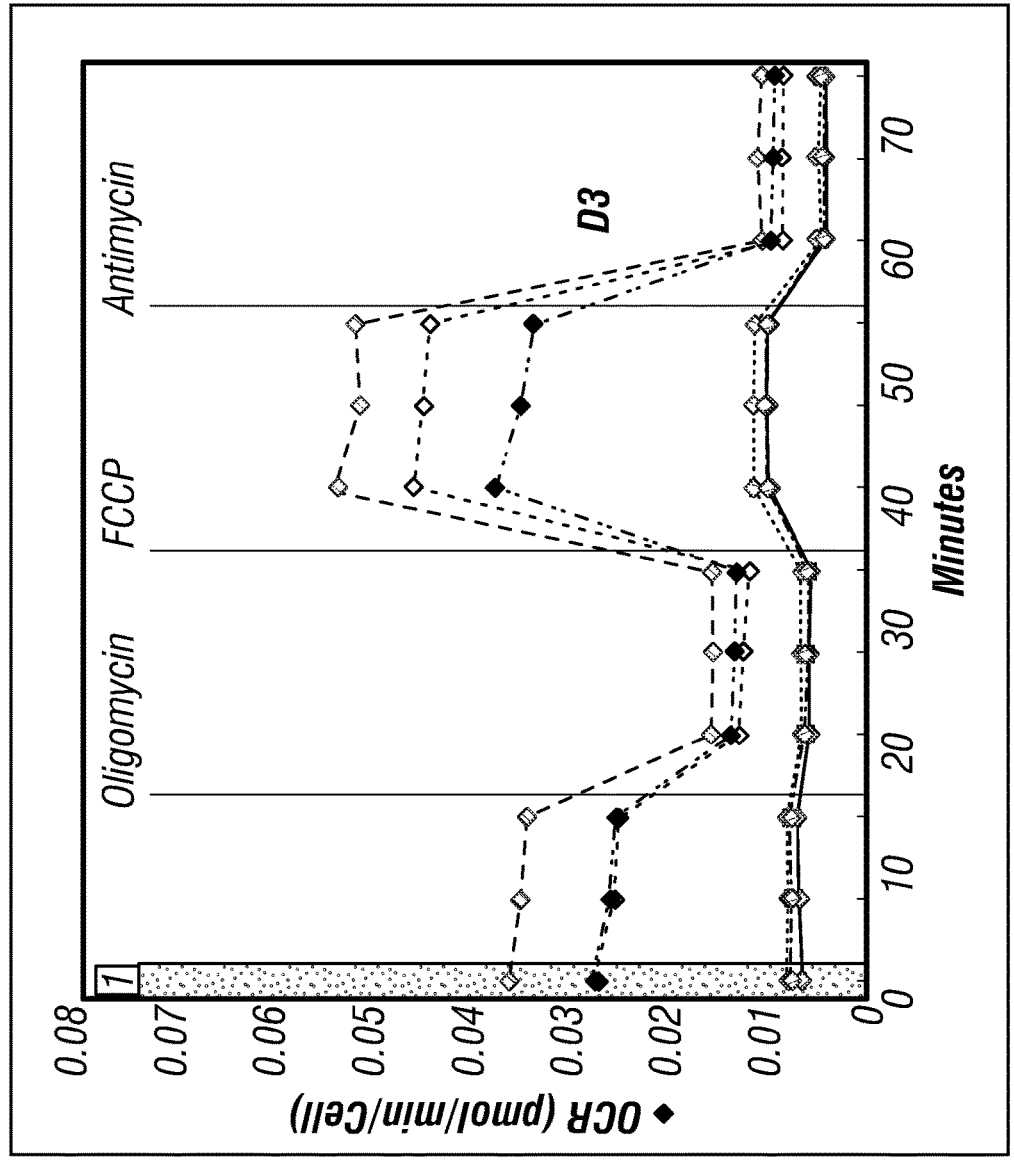
Figure 3B:
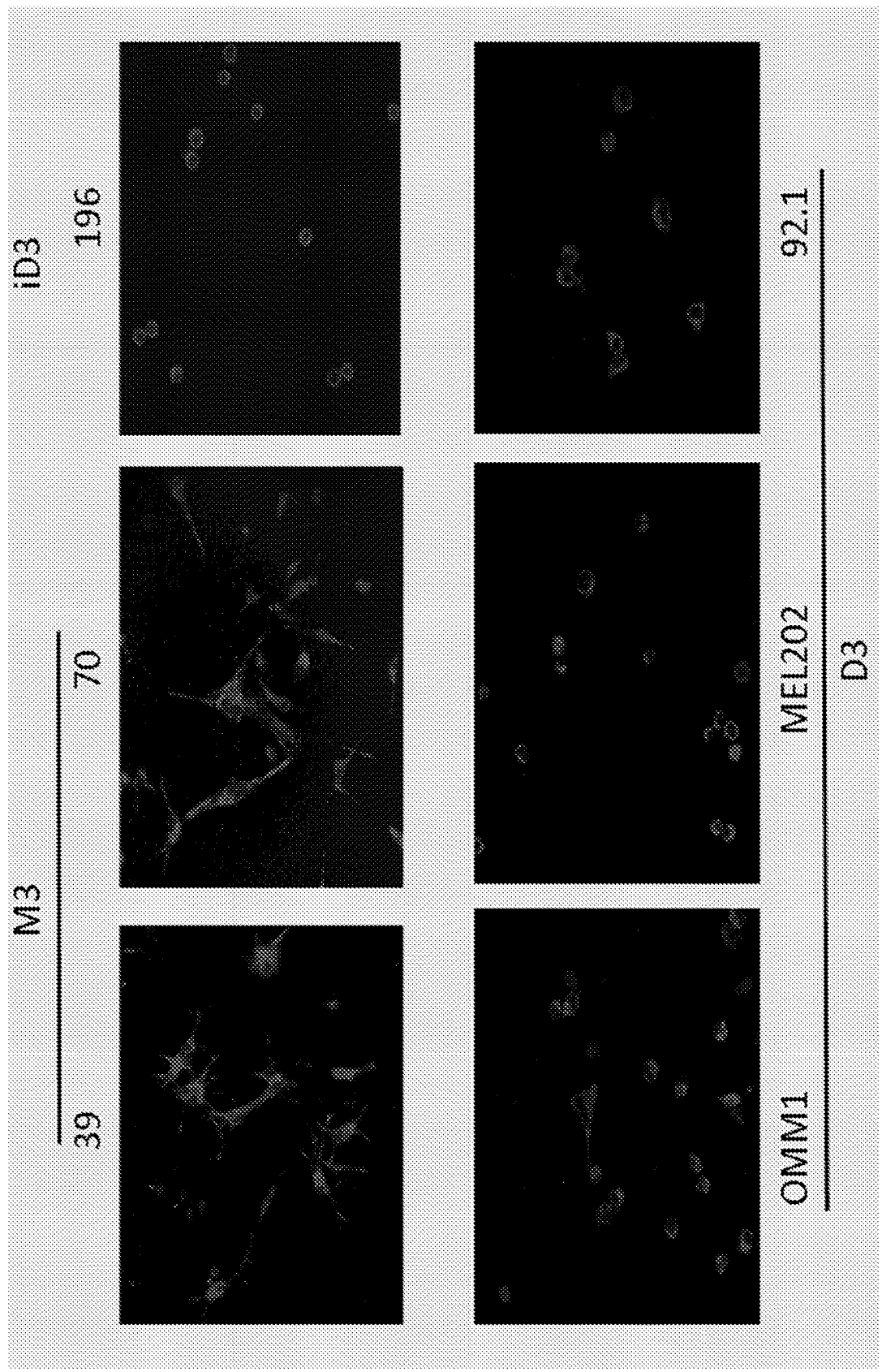
Figure 3C:
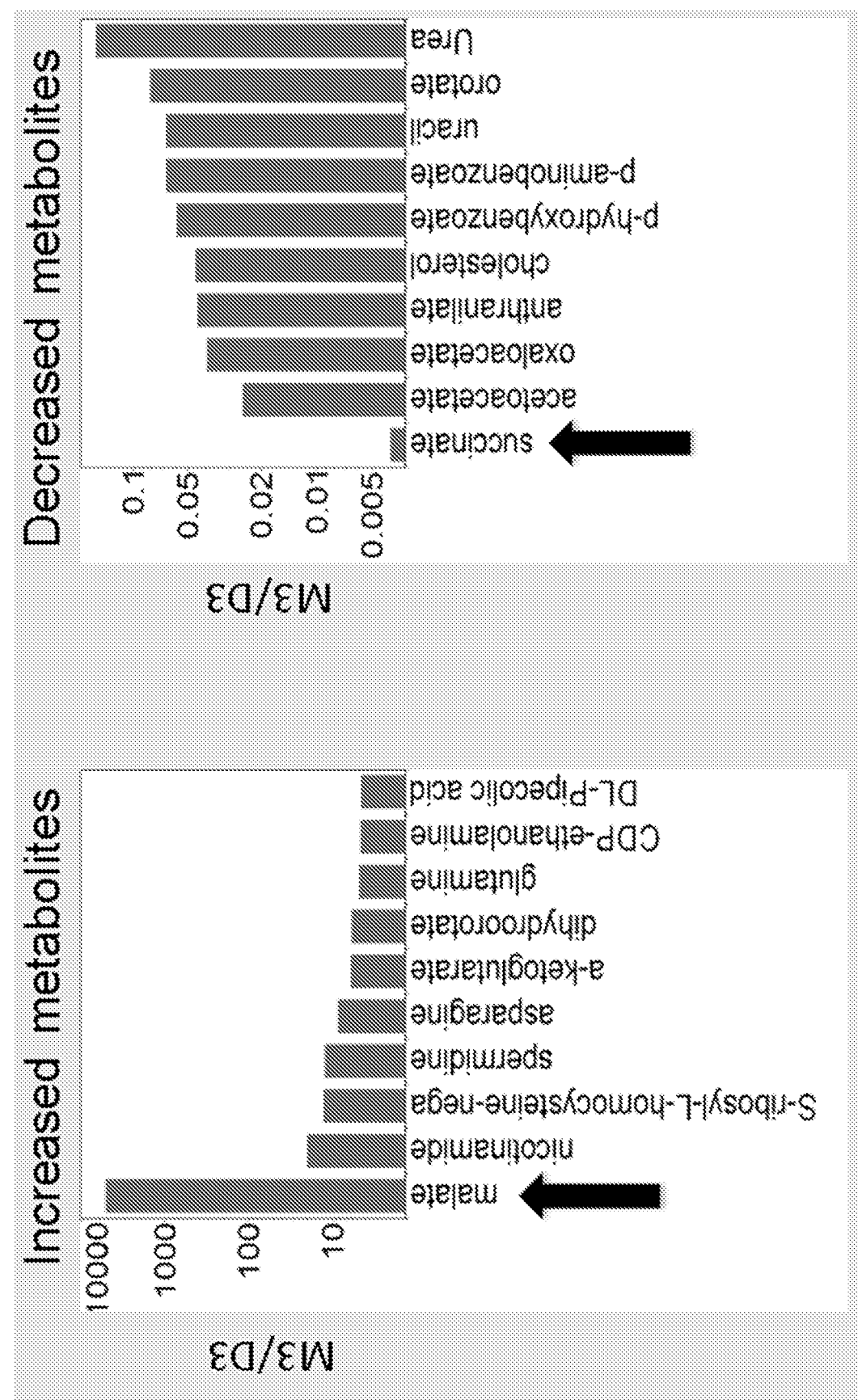

Mitochondrial reserve capacity was also measured in the uveal melanoma cell lines. It was found that the monosomy 3/BAP1 loss cells (left) have a higher mitochondrial reserve capacity as compared to the disomy 3/BAP1 normal (right) uveal melanoma cells (FIG. 3A). The greater mitochondrial content of the monosomy 3 cells was confirmed by immunofluorescence staining (FIG. 3B). In addition, the metabolic profile of the monosomy 3 uveal melanoma cells differed from the disomy 3 uveal melanoma cells (FIG. 3C). Metabolic profile analysis with mass spectrometric methods was followed by Ingenuity Pathway Analysis. Specifically, the monosomy 3 cells had higher malate and lower succinate as compared to the disomy 3 cells.

Figure 3D:
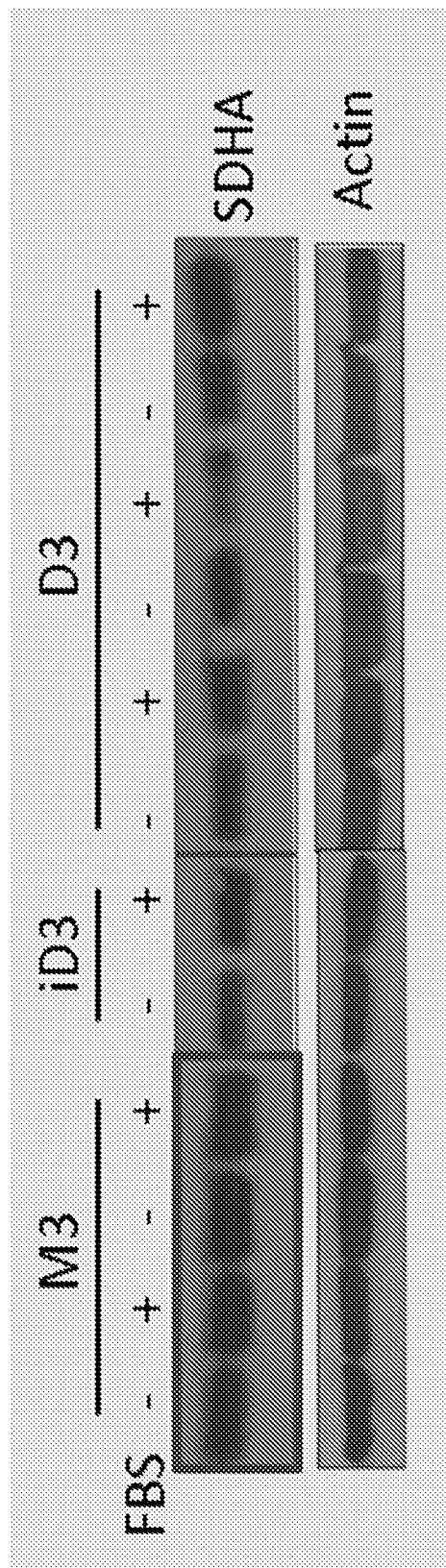
Figure 4:
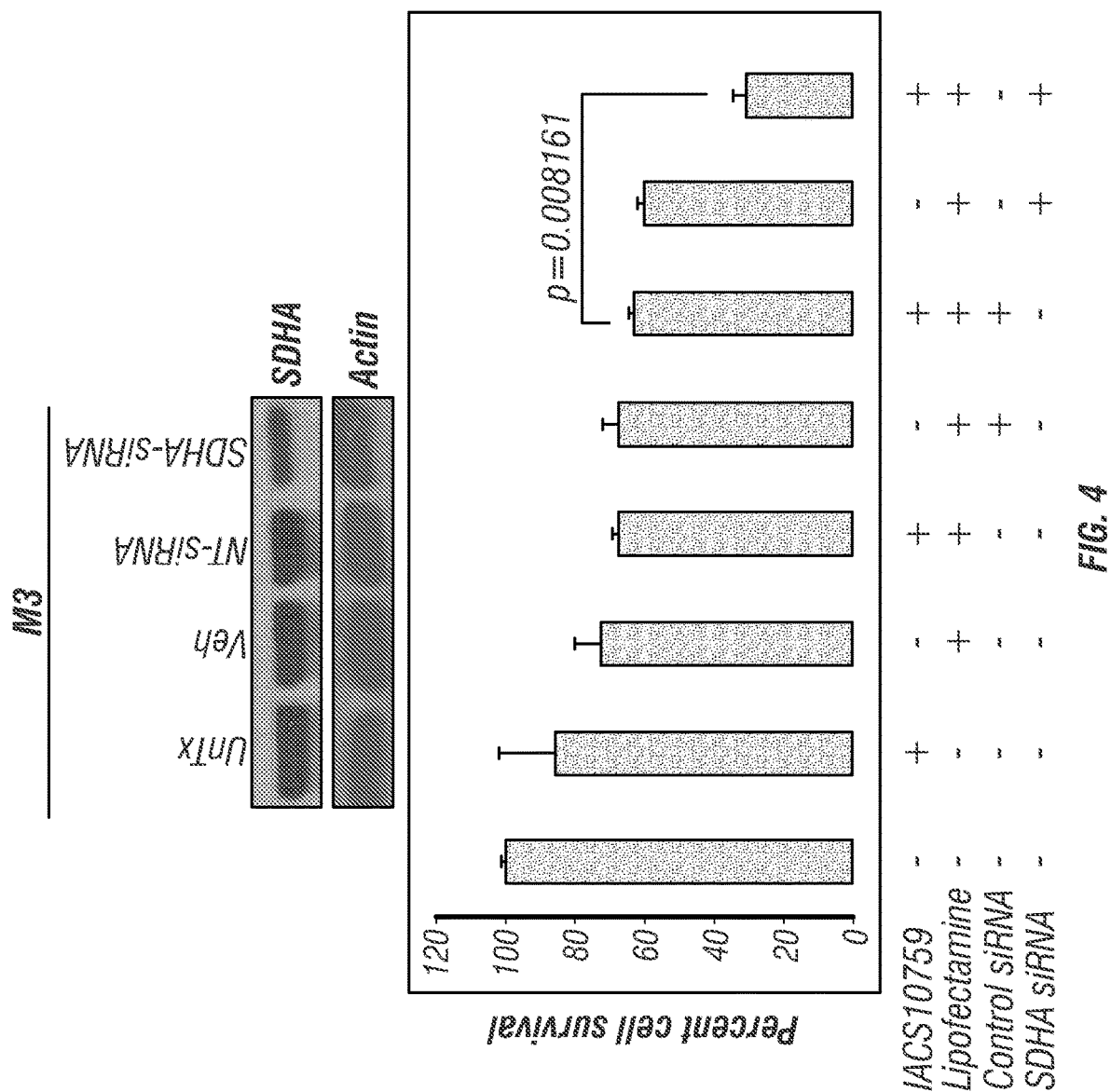
FIG. 4: Knockdown of SDHA expression with siRNA transfection decreases SDHA expression and sensitize monosomy 3 uveal melanoma cells to OXPHOS inhibition (IACS-10759).
Figure 5A:
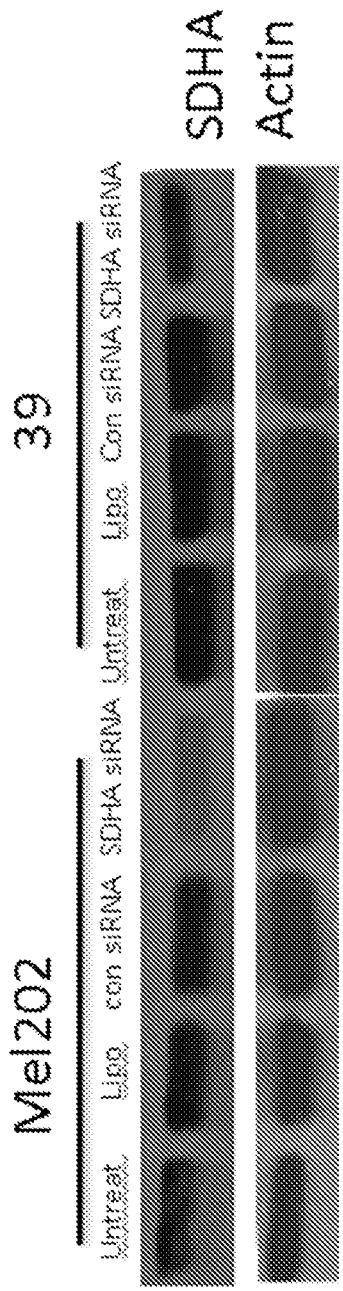
FIGS. 5A-5C: Effect of SDHA knockdown on monosomy 3 and disomy 3 cell lines, 39 and Me1202, respectively.
Figure 5B:
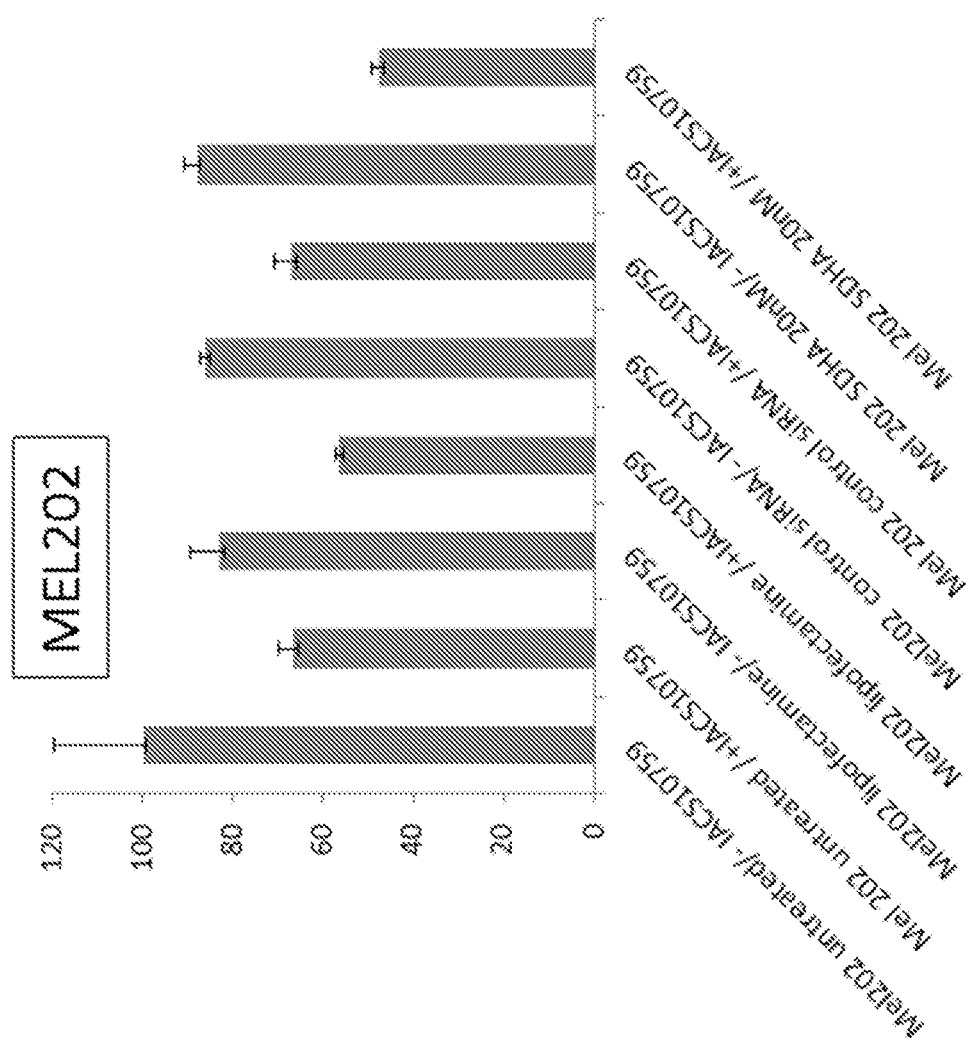
Figure 5C:
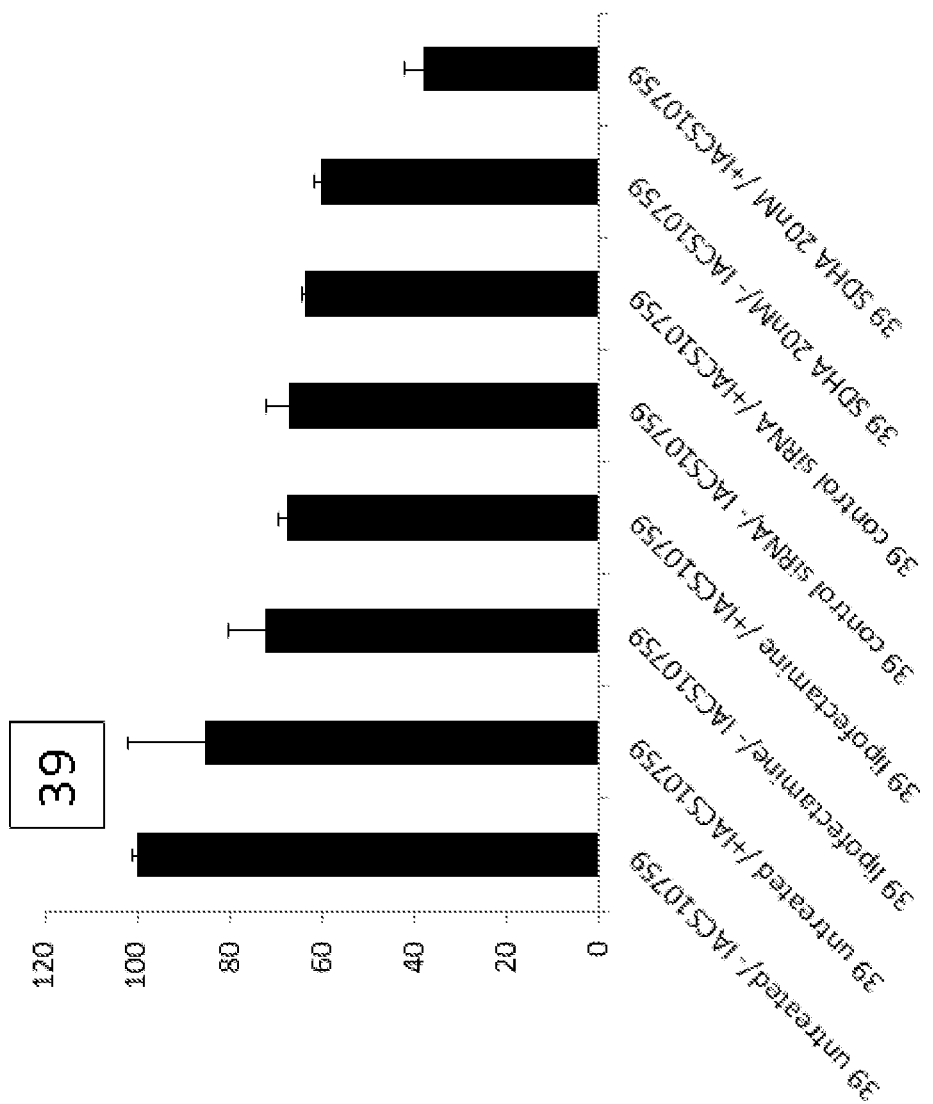

As SDHA expression was found to be upregulated in these monosomy 3 uveal melanoma cell lines (FIG. 3D), analysis was performed using SDHA siRNA to knockdown SDHA expression in the different uveal melanoma cell lines. It was observed that decreased SDHA expression sensitizes the monosomy 3 uveal melanoma cells to OXPHOS inhibition (IACS-10759) (FIG. 4). This sensitization to OXPHOS inhibition by knocking down SDHA expression was confirmed in the 39 cell lines and the Me1202 cell line with IACS-10759 treatment (FIGS. 5B-5C).

Figure 6:
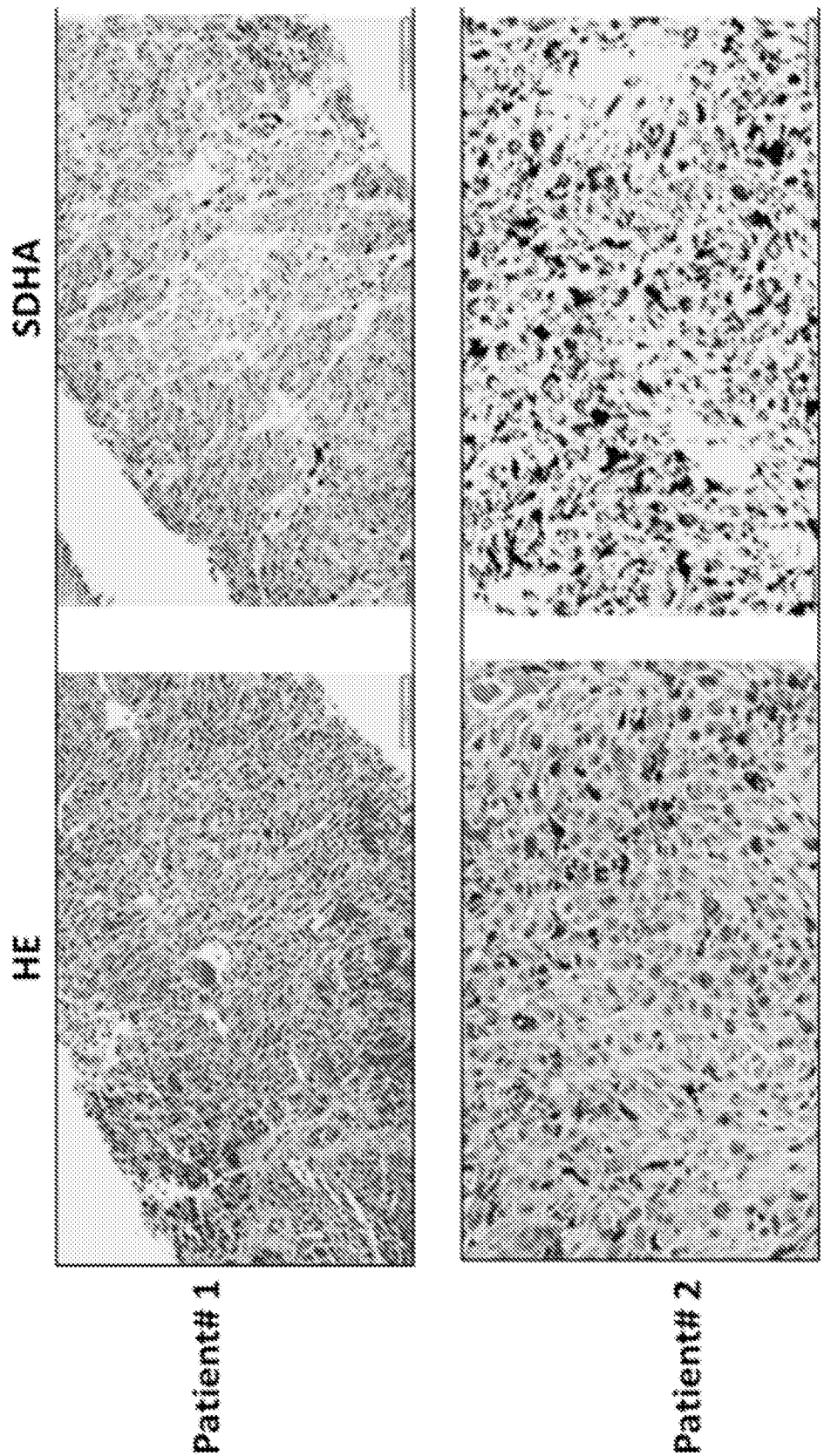
FIG. 6: Immunohistochemical staining of SDHA in non-responder patient tissue samples from uveal melanoma patients treated with ipilumab and nivolimumab checkpoint blockade therapy. SDHA is highly expressed in non-responders.
Figure 7A:
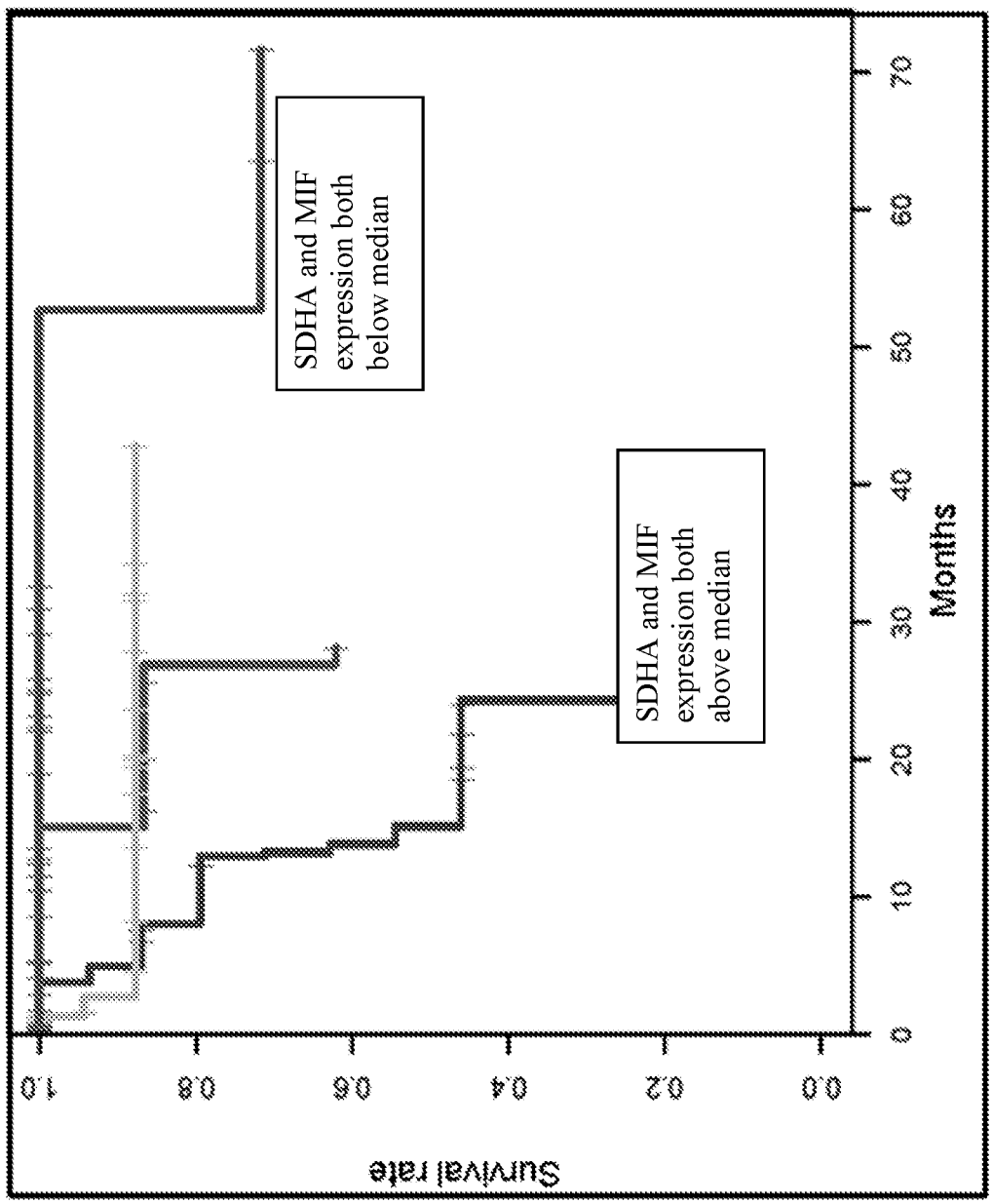
FIGS. 7A-7B.
Figure 7B:
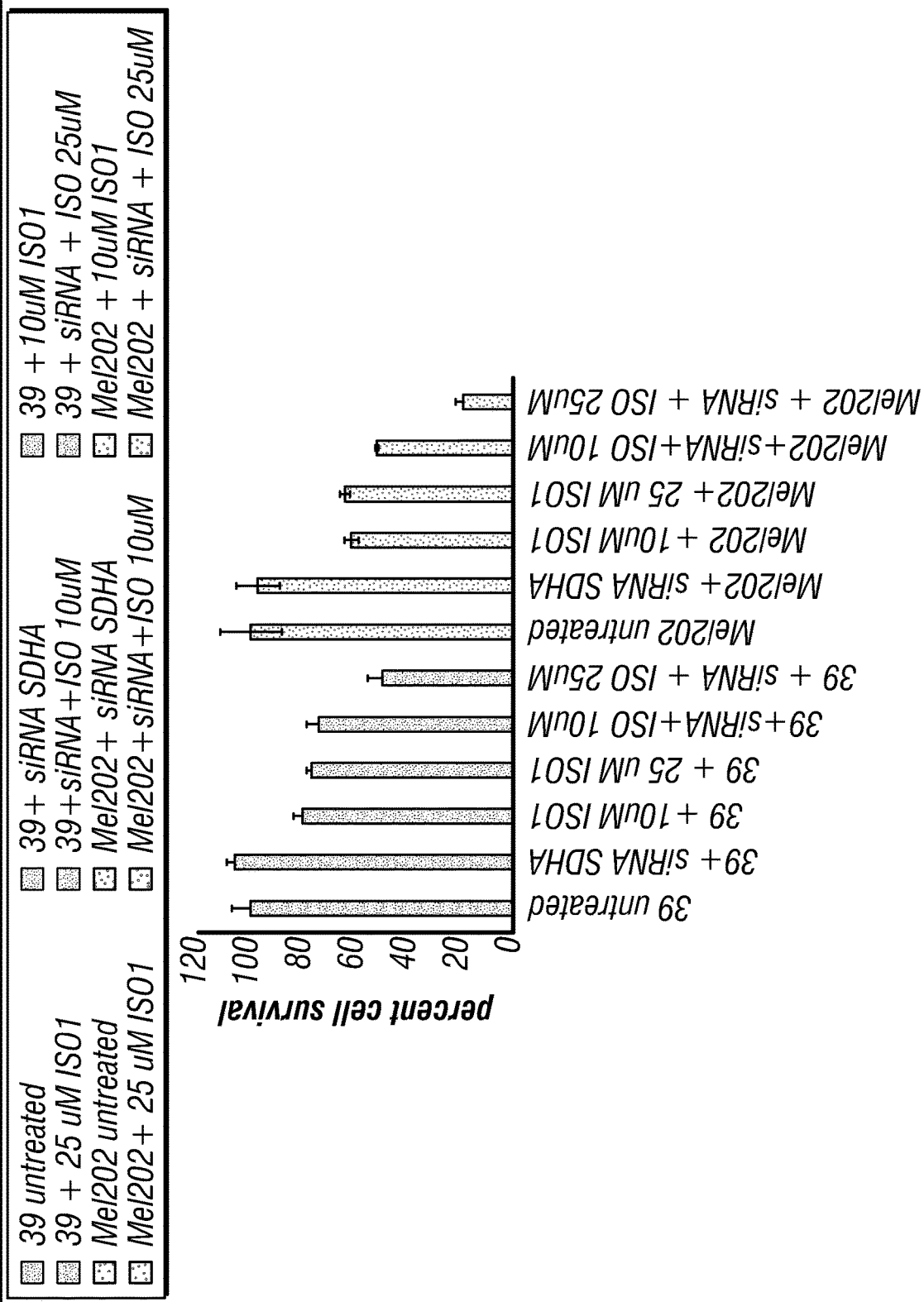
Figure 8A:
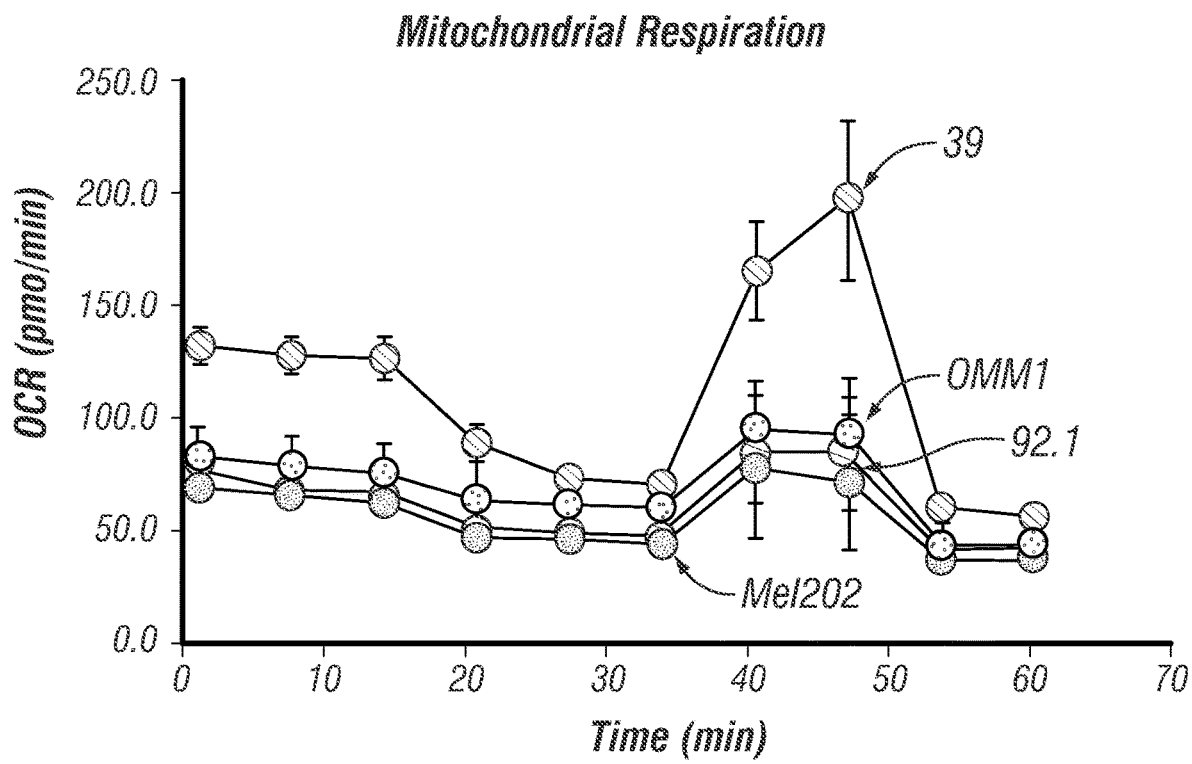
FIGS. 8A-8B.
Figure 8B:
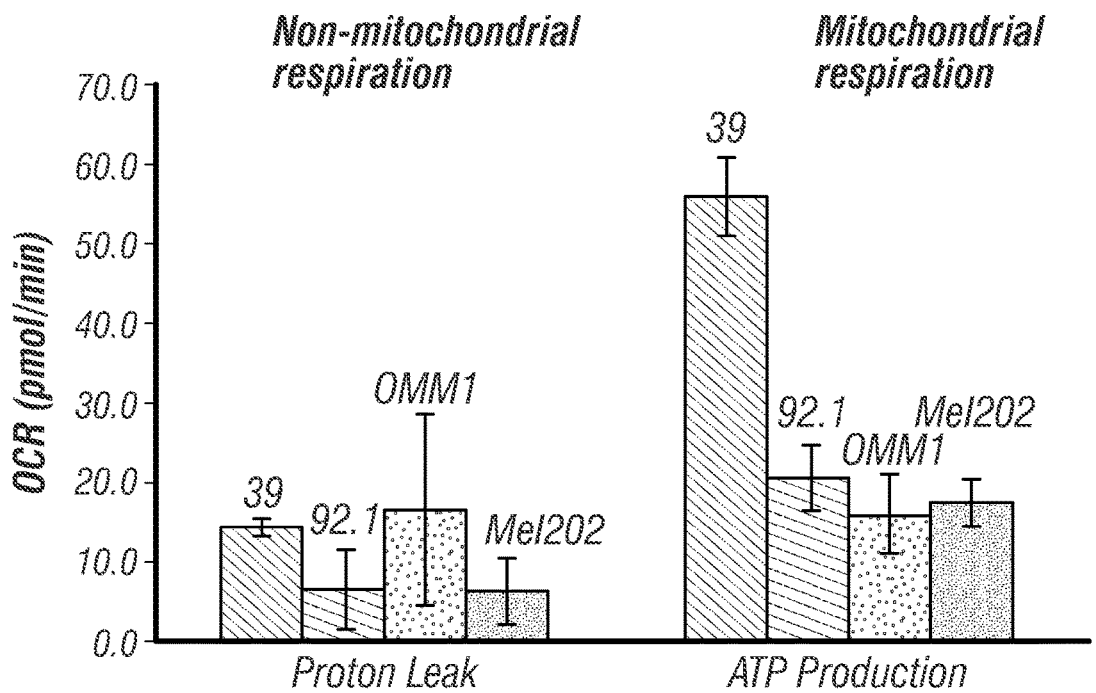

Patient samples were obtained from uveal melanoma patients treated with ipilumab and nivolimumab checkpoint blockade therapy Immunohistochemistry was performed on the patient samples for SDHA expression and it was found that SDHA was highly expressed in non-responders (FIG. 6). Accordingly, the survival rate of uveal melanoma was predicted using TCGA data of SDHA and/or MIF expression. SDHA and MIF expression both above median was associated with lowest survival rate (FIG. 7A). On the other hand, SDHA and MIF both below median was associated with highest survival rate. Thus, both SDHA and MIF expression correlate with survival rate of uveal melanoma patients and may be used for prognosis. The association of SDHA and MID with uveal melanoma survival rate was validated by measuring percent cell survival in monosomy 3 and disomy 3 cells treated with SHDA and/or MIF inhibitors. SDHA was inhibited by 20 nM siRNA and MIF was inhibited by 10 or 25 µM ISO-1. It was found that simultaneous inhibition of both SDHA and MIF resulted in the highest decrease in percent cell survival in both cell lines (FIG. 7B).

In conclusion, monosomy 3 cells were found to possess higher mitochondrial content, show lower sensitivity to OXPHOS inhibition, and display greater mitochondrial OXPHOS reserve capacity. In addition, the monosomy 3 cells have a metabolic profile consistent with increased ETC Complex II activity. Thus, both SDHA and MIF may be used for prognosis as well as therapy of uveal melanoma, particularly monosomy 3 uveal melanoma.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Ausubel et al., Current Protocols in Molecular Biology, John Wiley & Sons, New York, N.Y., 2003.
Field et al., Clin Cancer Res, 22(5):1234-412, 2016.
Godfrey et al., J. Mol. Diag. 2:84-91, 2000.
Heid et al, Genome Research 6:986-994, 1996.
International Patent Application No. WO2001014424
International Patent Publication No. WO 00/37504
International Patent Publication No. WO 01/14424
International Patent Publication No. WO 91117424
International Patent Publication No. WO 98/42752
International Patent Publication No. WO1995001994
International Patent Publication No. WO1998042752
International Patent Publication No. WO2000037504
International Patent Publication No. WO2006/121168
International Patent Publication No. WO2009/101611
International Patent Publication No. WO2009/114335
International Patent Publication No. WO2010/027827
International Patent Publication No. WO2011/066342
International Patent Publication No. WO2013131962
International Patent Publication No. WO2015016718
Leal, M., Ann NY Acad Sci 1321, 41-54, 2014.
Pardoll, Nature Rev Cancer, 12:252-264, 2012.
Sambrook et al., Molecular Cloning: A Laboratory Manual, Cold Spring Harbor Press, Cold Spring Harbor, N.Y., 1989.
Specht et al., Am. J. Pathol. 158:419-29, 2001.
Teicher, B. A. Current cancer drug targets 9, 982-1004, 2009.
U.S. Patent Application No. 20110008369
U.S. Patent Application No. 2014022021
U.S. Patent Application No. 20140294898
U.S. Pat. No. 4,870,287

U.S. Pat. No. 4,897,355
U.S. Pat. No. 4,946,787
U.S. Pat. No. 5,049,386
U.S. Pat. No. 5,538,848
U.S. Pat. No. 5,716,784
U.S. Pat. No. 5,723,591
U.S. Pat. No. 5,760,395
U.S. Pat. No. 5,844,905
U.S. Pat. No. 5,885,796
U.S. Pat. No. 6,207,156
U.S. Pat. No. 7,473,767
U.S. Pat. No. 8,008,449
U.S. Pat. No. 8,017,114
U.S. Pat. No. 8,119,129
U.S. Pat. No. 8,329,867
U.S. Pat. No. 8,354,509
U.S. Pat. No. 8,535,889
U.S. Pat. No. 8,735,553
U.S. Patent Publication No. 2005/0260186
U.S. Patent Publication No. 2006/0104968
U.S. Patent Publication No. US20130259858
U.S. Patent Publication No. US20140357660
U.S. Patent Publication No. US20160153042

What is claimed is:

1. A method of treating uveal melanoma in a human subject comprising:
   (a) determining the expression level of succinate dehydrogenase complex flavoprotein A (SDHA) in a sample from the subject;
   (b) identifying the subject as having Oxidative Phosphorylation (OXPHOS) resistant uveal melanoma by detecting elevated SDHA as compared to a control; and
   (c) administering an effective amount of an SDHA inhibitor in combination with an OXPHOS inhibitor to said subject to overcome resistance to the OXPHOS inhibitor.

2. The method of claim 1, wherein the elevated expression of SDHA was determined by RT-qPCR, RNA-sequencing or microarray analysis performed on RNA isolated from a sample from the human subject.

3. The method of claim 2, wherein the sample is a tissue biopsy, fine needle aspirate, saliva, urine, or plasma.

4. The method of claim 2, wherein the sample is a tissue biopsy.

5. The method of claim 4, wherein the tissue biopsy is further defined as formalin fixed paraffin embedded (FFPE) tissue.

6. The method of claim 4, wherein the tissue biopsy is further defined as a tumor biopsy.

7. The method of claim 1, wherein the human subject has an elevated expression of MIF as compared to a non-cancerous control.

8. The method of claim 2, further comprising detecting the expression of one or more genes selected from the group consisting of BAP1_varA, BAP1_varB, MGP, SPP1, CXCL14, CLCA2, S100A8, BTG1, SAP130, ARG1, KRT6B, GJA, ID2, EIF1B, S100A9, CRABP2, KRT14, ROBOT, RBM23, TACSTD2, DSC1, SPRR1B, TRIM29, AQP3, TYRP1, PPL, LTA4H, and CST6.

9. The method of claim 1, wherein the human subject has previously been administered or is being administered an anti-cancer therapy.

10. The method of claim 9, wherein the anti-cancer therapy is chemotherapy, immunotherapy, surgery, radiotherapy, or biotherapy.

11. The method of claim 1, wherein the OXPHOS inhibitor is IACS-1131, IACS-10759, oligomycin, rotenone, or metformin.

12. The method of claim 3, wherein the uveal melanoma is metastatic melanoma.

13. The method of claim 3, wherein the human subject has monosomy 3 and/or BAP1 loss.

14. The method of claim 1, wherein the SDHA inhibitor is an inhibitory nucleic acid.

15. The method of claim 14, wherein the inhibitory nucleic acid is siRNA, shRNA, or miRNA.

16. The method of claim 1, wherein the SDHA inhibitor and OXPHOS inhibitor are delivered simultaneously.

17. The method of claim 1, wherein the uveal melanoma is further defined as BAP1 loss uveal melanoma.

18. The method of claim 8, wherein BAP1_varA and BAP1_varB have decreased expression as compared to a non-cancerous control.

* * * * *